(12) United States Patent
Boudreaux

(10) Patent No.: US 10,092,348 B2
(45) Date of Patent: Oct. 9, 2018

(54) RF TISSUE SEALER, SHEAR GRIP, TRIGGER LOCK MECHANISM AND ENERGY ACTIVATION

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 642 days.

(21) Appl. No.: 14/579,599

(22) Filed: Dec. 22, 2014

(65) Prior Publication Data

US 2016/0175030 A1 Jun. 23, 2016

(51) Int. Cl.
*A61B 18/14* (2006.01)
*A61B 18/00* (2006.01)
*A61B 17/00* (2006.01)

(52) U.S. Cl.
CPC ...... *A61B 18/1442* (2013.01); *A61B 2017/00438* (2013.01); *A61B 2018/0063* (2013.01); *A61B 2018/00589* (2013.01); *A61B 2018/00922* (2013.01); *A61B 2018/146* (2013.01); *A61B 2018/1455* (2013.01)

(58) Field of Classification Search
CPC .......... A61B 17/285; A61B 17/29; A61B 17/320092; A61B 18/1206; A61B 18/1445; A61B 18/1815; A61B 2017/2946; A61B 2018/00196; A61B 2018/00916;

(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 2868227 Y 2/2007
CN 102834069 A 12/2012
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Amanda Patton

(57) ABSTRACT

A variety of surgical instruments include one or more elements that transmit RF energy to tissue. Some such instruments comprise a pair of jaws that open and close on tissue, with conductive tissue contact surfaces that are operable to weld tissue clamped between the jaws. Some surgical instruments also include a translating tissue cutting element. Some such instruments may be in the form of forceps having a scissor grip. Forceps type instruments may in some instances provide a feature that allows the jaws of the forceps to be locked on tissue, so that the operator can remove his or her hands from the instrument. In such an instrument it may also be desirable to provide a circuit that is activated only when the forceps are closed and sufficient pressure is applied to the tissue between the jaws of the device.

25 Claims, 24 Drawing Sheets

(58) Field of Classification Search
CPC .... A61B 2018/1455; A61B 2018/1807; A61B 2018/4857
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,314,559 A | 2/1982 | Allen |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |

(56) References Cited

U.S. PATENT DOCUMENTS

| | | |
|---|---|---|
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| 6,409,722 B1 | 6/2002 | Hoey et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B2 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,610,060 B2 | 8/2003 | Mulier et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,682,501 B1 | 1/2004 | Nelson et al. |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |

(56) References Cited

U.S. PATENT DOCUMENTS

| | | |
|---|---|---|
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,056,787 B2 | 11/2011 | Boudreaux et al. |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |

(56) References Cited

U.S. PATENT DOCUMENTS

| | | |
|---|---|---|
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,608,044 B2 | 12/2013 | Hueil et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,017,372 B2 * | 4/2015 | Artale .................. A61B 17/285 606/167 |
| 9,028,494 B2 | 5/2015 | Shelton, IV et al. |
| 9,028,519 B2 | 5/2015 | Yates et al. |
| 9,039,731 B2 | 5/2015 | Joseph |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |

(56) References Cited

U.S. PATENT DOCUMENTS

| | | |
|---|---|---|
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0257680 A1* | 10/2011 | Reschke .......... A61B 17/285 606/206 |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Homer |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |

(56) References Cited

U.S. PATENT DOCUMENTS

| | | |
|---|---|---|
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194874 A1 | 7/2014 | Dietz et al. |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |

(56) References Cited

FOREIGN PATENT DOCUMENTS

| WO | WO 99/40861 A1 | 8/1999 |
|---|---|---|
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/044343 A2 | 4/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=joumal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_V10_200_S D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
U.S. Appl. No. 12/576,529, filed Oct. 9, 2009.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.

* cited by examiner

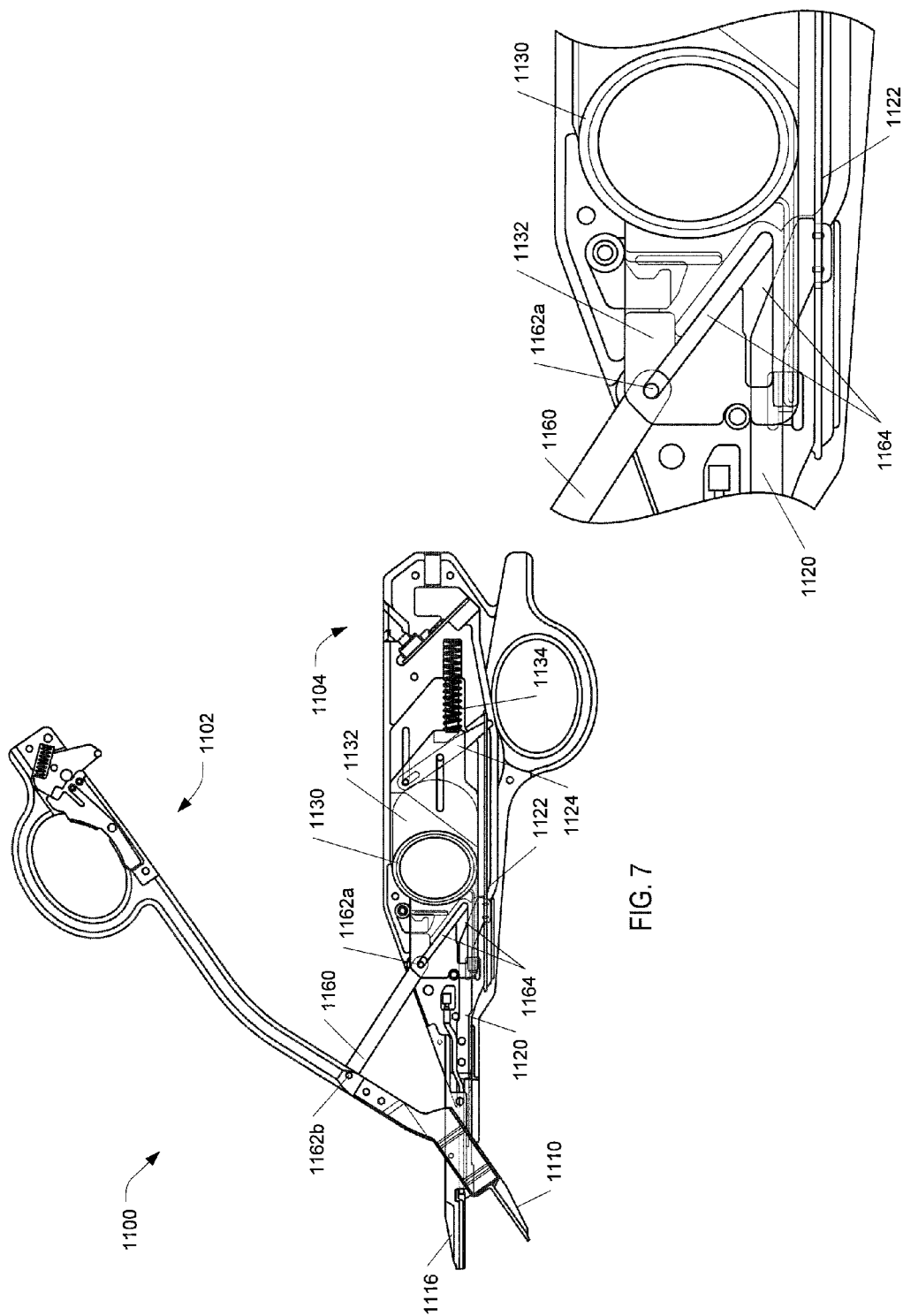

RF TISSUE SEALER, SHEAR GRIP, TRIGGER LOCK MECHANISM AND ENERGY ACTIVATION

INTRODUCTION

The present disclosure relates generally to a radio frequency (RF) cutting forceps and various mechanism associated therewith.

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue.

When an electrosurgical instrument includes grasping jaws and tissue severing capabilities it may be desirable to avoid accidental cutting by the knife. Hence, the instrument may include a feature that prevents the knife from firing until the jaws are sufficiently closed upon the tissue. It may also be desirable to prevent the jaws from being opened until the knife has been retracted. One or both of these features can prevent the knife from being extended while the jaws are open.

Forceps type instruments may in some instances provide a feature that allows the jaws of the forceps to be locked on tissue, so that the operator can remove his or her hands from the instrument. In such an instrument it may also be desirable to provide a circuit that is activated only when the forceps are closed and sufficient pressure is applied to the tissue between the jaws of the device.

SUMMARY

In one embodiment, an electrosurgical instrument for operating on tissue comprises a first arm, comprising a first handle and a first jaw. A second arm is pivotally connected to the first arm. The second arm comprises a second handle; a second jaw comprising an electrode operable to deliver radio frequency (RF) energy to tissue; a knife configured to translate within slots defined in the first and second jaws; and a push plate operably connected to the knife such that a proximal motion of the push plate extends the knife and a distal motion of the push plate retracts the knife. A trigger lock mechanism comprises a switch arm pivotally mounted to the first arm, the switch arm comprising a first end and a second end, wherein the first end extends below the first arm, the trigger lock mechanism configured to prevent the first and second jaw from being opened.

In one embodiment, the electrosurgical instrument comprises a pull ring integrated into the push plate for operating the knife.

In one embodiment of the electrosurgical instrument, the first end of the switch arm comprises a protrusion.

In one embodiment of the electrosurgical instrument the trigger lock mechanism comprises a slot integrated into the lower arm and configured to accept the first end of the switch arm, the slot comprising a guide configured to direct the first end of the switch arm in a distal direction, the slot further comprising a lip at the distal side, the lip configured to prevent the first end of the switch arm from exiting the slot. The guide of the electrosurgical instrument comprises a ramp upon which the protrusion rides.

In one embodiment, the electrosurgical instrument comprises a lock spring, wherein the second end of the switch arm rests against the lock spring and wherein the lock spring is configured to return the switch arm to a neutral position.

In one embodiment of the electrosurgical instrument, the first end of the switch arm comprises a lock button pivotally mounted inside the first handle and wherein the switch arm is movable between a first position and a second position, wherein the second position prevents the switch arm from returning to a neutral position. The switch arm of the electrosurgical instrument may be configured to prevent the lock button from transitioning between the first position and the second position when the switch arm is in the neutral position.

In one embodiment of the electrosurgical instrument, the second arm further comprises an energy button configured to activate the RF energy.

In another embodiment, an electrosurgical instrument for operating on tissue comprises a first arm comprising a first handle and a first jaw; a second arm pivotally connected to the first arm. The second arm comprising a second handle; a second jaw comprising an electrode operable to deliver radio frequency (RF) energy to tissue; a knife configured to translate within slots defined in the first and second jaws; a push plate operably connected to the knife such that a proximal motion of the push plate extends the knife and a distal motion of the push plate retracts the knife; and a trigger lock mechanism configured to prevent the first and second jaw from being opened. The second arm further comprises a compression circuit and a compression button for activating the compression circuit. The compression button is located at the base of the switch arm slot and is activated by pressure applied by the switch arm.

In one embodiment, the electrosurgical instrument comprises a pull ring integrated into the push plate for operating the knife.

In one embodiment of the electrosurgical instrument the second arm comprises an energy button. The energy button of the electrosurgical instrument may be configured to activate the RF energy and the compression circuit is configured to enable an end tone. The RF energy of the electrosurgical instrument may be activated only when both the energy button and the compression circuit are activated simultaneously. The energy button of the electrosurgical instrument may be configured to activate the RF energy and the compression circuit may be configured to activate the RF energy.

In one embodiment of the electrosurgical instrument the compression circuit may be configured to enable the RF energy.

In another embodiment, an electrosurgical instrument for operating on tissue comprises a first arm comprising a first handle and a first jaw; a second arm pivotally connected to the first arm, the second arm comprising a second handle; a second jaw comprising an electrode operable to deliver radio frequency (RF) energy to tissue; a knife configured to translate within slots defined in the first and second jaws; a push plate operably connected to the knife such that a proximal motion of the push plate extends the knife and a distal motion of the ring retracts the knife; a compression circuit; and a compression circuit button configured to activate the compression circuit.

In one embodiment, the electrosurgical instrument comprises a pull ring integrated into the push plate for operating the knife.

In one embodiment, the electrosurgical instrument comprises a switch arm pivotally mounted to the first arm, the switch arm comprising a first end and a second end, wherein the first end extends below the first arm; and a switch arm slot integrated into the lower arm and configured to accept the first end of the switch arm; wherein the compression button is located at the base of the switch arm slot and is activated by pressure applied by the switch arm.

In one embodiment of the electrosurgical instrument the switch arm is configured to required extra pressure on the first arm for the switch arm to activate the compression button.

In one embodiment, the electrosurgical instrument comprises an energy button.

In one embodiment of the electrosurgical instrument the energy button may be configured to activate the RF energy and the compression circuit is configured to enable an end tone.

In one embodiment of the electrosurgical instrument the RF energy may be activated only when both the energy button and the compression circuit are activated simultaneously.

In one embodiment of the electrosurgical instrument the energy button may be configured to activate the RF energy and the compression circuit is configured to activate the RF energy.

In one embodiment of the electrosurgical instrument the compression circuit may be configured to enable the RF energy.

FIGURES

The novel features of the embodiments described herein are set forth with particularity in the appended claims. The embodiments, however, both as to organization and methods of operation may be better understood by reference to the following description, taken in conjunction with the accompanying drawings as follows:

FIG. 7 illustrates a sideways transparent view of one embodiment of a cutting forceps that comprises a knife lockout mechanism;

FIG. 8 illustrates a close-up transparent view of the knife lockout mechanism of the cutting forceps shown in FIG. 7;

DESCRIPTION

Figure 1:
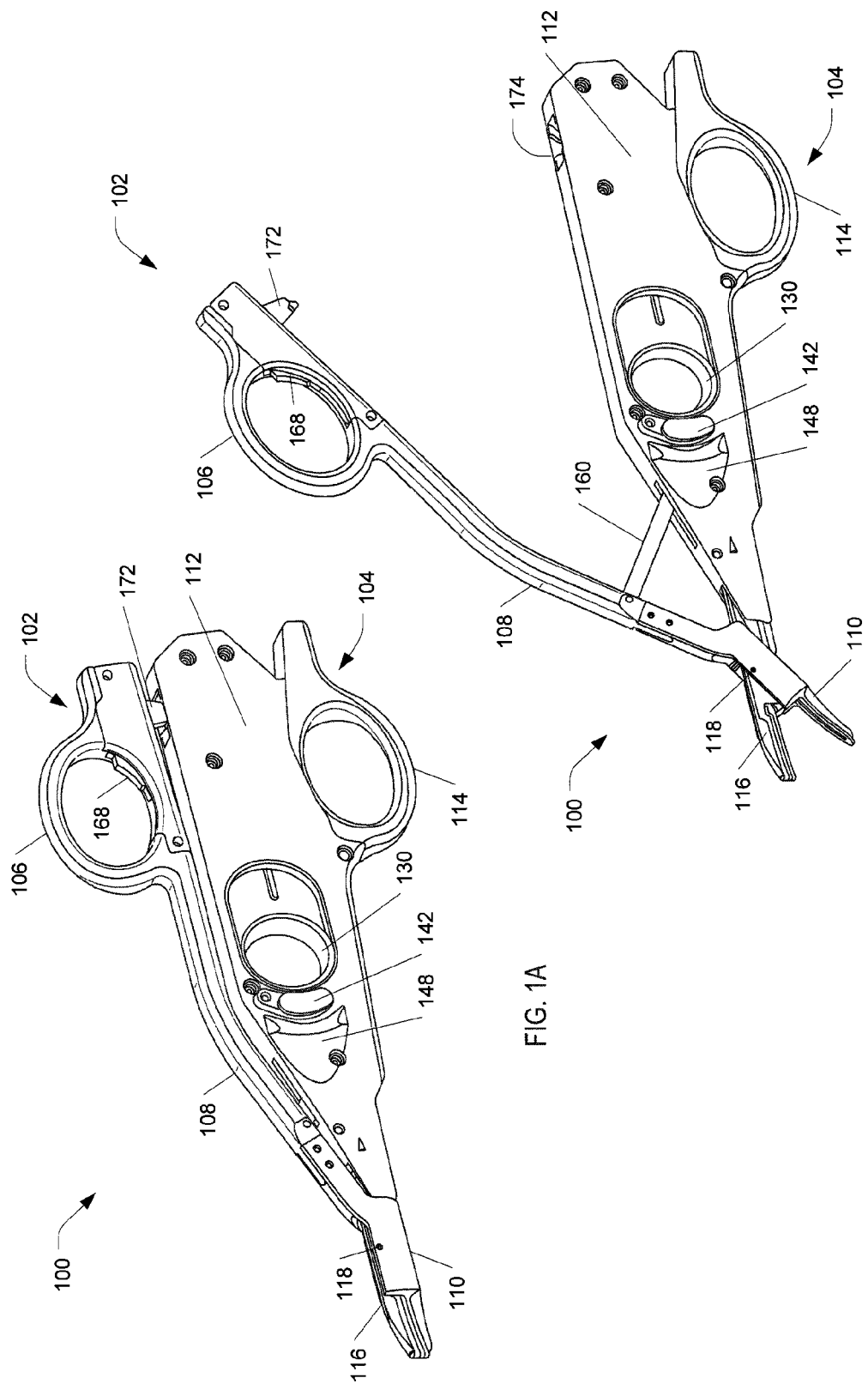
FIG. 1A illustrates a perspective view of one embodiment of an RF cutting forceps (also called a "cutting forceps") in a closed position.
FIG. 1B illustrates a perspective view of the cutting forceps shown in FIG. 1A in an open position.

The Applicant of the present application also owns the U.S. Patent Applications identified below which were filed on Dec. 22, 2014 and which are each herein incorporated by reference in their respective entireties:

U.S. patent application Ser. No. 14/579,623, entitled RF TISSUE SEALER, SHEAR GRIP, TRIGGER LOCK MECHANISM AND ENERGY ACTIVATION; and U.S. patent application Ser. No. 14/579,299, entitled TISSUE SEALING AND CUTTING INSTRUMENT WITH LOCKING FEATURES.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the RF cutting forceps in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

Also, in the following description, it is to be understood that terms such as front, back, inside, outside, top, bottom, upper, lower and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Overview of Electrosurgical Instrument

An electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handpiece may be positioned at the proximal end of the shaft for manipulating the end effector. Such a handpiece may have a pistol grip configuration or some other configuration.

In some instances, it may be desirable to provide an electrosurgical instrument that does not have an elongate shaft or handpiece similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pub. No. 2014/0214019, entitled "Electrosurgical Hand Shears," published Jul. 31, 2014, the disclosure of which is incorporated by reference herein. Various other examples of electrosurgical forceps instruments will be described in greater detail below; while other examples will be apparent to those of ordinary skill in the art in view of the teachings herein.

Various embodiments of electrosurgical shears or forceps with RF energy for sealing tissue may be provided. One such embodiment may provide a distal energy switch and a proximal energy switch. Such an embodiment may operate as follows: first, the jaws of the device are closed on tissue. Once the jaws are closed on tissue, the proximal energy switch may or may not be activated. Second, the distal energy switch is activated. Activation of the distal energy switch delivers RF energy to the tissue. In some embodiments, if the proximal energy switch has not been activated, a warning may be issued, such as for instance by an external generator that provides power to the device. Third, a processor, possibly located in the cutting forceps or possibly located in the power generator, determines when the tissue has been sufficiently heated to be sealed. Fourth, a tone or signal may be issued when it has been determined that the tissue is sealed and is ready to cut. If the proximal energy switch has not been activated the tone may not issue and/or a warning may be signaled. In some embodiments, the end tone is dependent on the impedance of the tissue between the jaws. Fifth, the distal energy button is released. Sixth, a knife cuts the tissue between the jaws by way of a knife trigger.

Seventh, the knife is returned to a starting position. Eight, the jaws are opened to release the tissue.

Another embodiment of an electrosurgical shears or forceps with RF energy for sealing tissue may provide a distal energy switch and a proximal energy switch. The operation of such an embodiment may be as follows: first, the jaws are closed on tissue. Once the jaws are closed on tissue, the proximal energy switch may or may not be activated. Second, the distal energy switch is activated. The RF energy will not be activated if the proximal energy switch has not been activated. A warning may be issued, such as by instance by the external generator. When the proximal energy switch is activated, thus activating the RF energy, then third, a processor, possibly located in the cutting forceps or possibly located in the power generator, determines when the tissue has been sufficiently heated to be sealed. Fourth, a tone or signal may be issued when it has been determined that the tissue is sealed and is ready to cut. In some embodiments, the end tone is dependent on the impedance of the tissue between the jaws. Fifth, the distal energy button is released. Sixth, a knife cuts the tissue between the jaws by way of a knife trigger. Seventh, the knife is returned to a starting position. Eight, the jaws are opened to release the tissue.

Another embodiment of an electrosurgical shears or forceps with RF energy for sealing tissue may provide a proximal energy switch. The operation of such an embodiment may be as follows: first, the jaws are closed on tissue. Once the jaws are closed on tissue, the proximal energy switch may or may not be activated. Second, the upper forceps arm may be closed and flexed to activate the proximal energy switch. A switch arm attached to the upper forceps arm may be configured to touch and activate the proximal energy switch. Third, a processor, possibly located in the cutting forceps or possibly located in the power generator, determines when the tissue has been sufficiently heated to be sealed. Fourth, a tone or signal may be issued when it has been determined that the tissue is sealed and is ready to cut. At the same time, the RF energy may be deactivated automatically, without deactivation of the proximal energy switch. Fifth, a knife cuts the tissue between the jaws by way of a knife trigger. Sixth, the knife is returned to a starting position. Seventh, the jaws are opened to release the tissue.

Cutting Forceps

One embodiment of an RF cutting forceps comprises a first or upper arm pivotally connect to a second or lower arm. The upper arm comprises a first or upper handle ring and a first or lower jaw. The lower arm comprises a second or lower handle ring, a lower arm body, and a second or upper jaw. The lower arm body comprises a pull ring operatively connected to a knife. The knife is configured to translate distally between the jaws to sever tissue held by the jaws.

Another embodiment of an RF cutting forceps comprises the upper and lower arms as descried above, and additionally comprises a knife lockout mechanism. The knife lockout mechanism comprises a movement arm and a slot. The slot is integrated into a push plate, which also comprises the pull ring. The movement arm is pivotally connected at a first end to the upper arm and is driven by the upper arm as the upper arm opens and closes. At the second end of the movement arm is a lower movement arm pin that rides in the slot. In some embodiments, the upper portion of the slot is positioned at an angle that prevents the pull ring from being drawn so long as the lower movement arm pin is within the upper portion of the slot. In some embodiments, the lower portion of the slot is positioned horizontally to the direction of motion of the pull ring. In such embodiments, the pull ring can be drawn when the lower movement arm pin is in the lower portion of the slot, but the jaws cannot be opened so long as the lower movement arm pin is located in the lower portion of the slot.

Another embodiment of an RF cutting forceps comprises the upper and lower arms as described above, and additionally comprises a trigger lockout mechanism. The trigger lockout mechanism comprises a lock button, a switch arm, and a switch arm slot. The switch arm comprises a first end that extends below the upper arm. The switch arm slot is positioned within the lower arm body to receive the first end of the switch arm. In some embodiments, the switch arm slot may comprise a guide or ramp that causes the switch arm to pivot such that the first end can be trapped by a lip within the switch arm slot. The lock button may be configured to maintain the locked position of the switch arm slot. In some embodiments, the RF cutting forceps also comprises a compression circuit that is activated by a compression circuit button. In such embodiments, the compression circuit button is positioned at the base of the switch arm slot, such that it can be activated by the pressure applied by the switch arm.

FIG. 1A illustrates a perspective view of one embodiment of an RF cutting forceps 100 (also called a "cutting forceps") in a closed position. The cutting forceps 100 comprises an upper arm 102 and a lower arm 104 pivotally connected at a pivot joint 118 near the distal end of the device. The upper 102 and lower arm 104 are shaped such that the cutting forceps 100 can be operated by either a left-handed or right-handed person. The cutting forceps 100 can also be operated as illustrated or upside down from how it is illustrated. As such, the terms upper and lower and left and right are used for convenience only, and not as a limitation.

The upper arm 102 comprises a first or upper handle ring 106 near the proximal end of the upper arm 102, a bend arm 108 between the proximal and distal ends, and a first or lower jaw 110 at the distal end. The upper handle ring 106 is shaped such that a human finger can be inserted therein. In some embodiments, the upper handle ring 106 comprises a lock button 168 and switch arm 172, described in further detail below. The bend arm 108 connects the upper handle ring 106 to the lower jaw 110. The upper handle ring 106, bend arm 108, and lower jaw 110 are connected in a fixed orientation, such that as the upper handle ring 106 is moved all parts of the upper arm 102 move together.

The lower arm 104 comprises a lower arm body 112 and a second or upper jaw 116. Integrated with the proximal end of the lower arm body 112 is a second or lower handle ring 114. The lower handle ring 114 is shaped such that a human finger can be inserted therein. The distal end of the lower arm body 112 is connected to the upper jaw 116. The lower arm body 112, the lower handle ring 114, and the upper jaw 116 are connected in a fixed orientation, such that all parts of the lower arm 104 move together. The lower arm body 112 further comprises a pull ring 130 for controlling the operation of the knife 120, described in further detail below. In some embodiments the lower arm body 112 also comprises an energy button 142 for activating the RF energy, also described in further detail below. The lower arm body 112 also comprises a bump 148 that prevents accidental activation of the energy button 142.

FIG. 1B illustrates a perspective view of the cutting forceps 100 shown in FIG. 1A in an open position. As explained above, the upper arm 102 is pivotally connected at a pivot joint 118 to the lower arm 104 near the distal end of the cutting forceps 100. As the upper arm 102 is raised, the proximal end of the upper arm 102 pivots away from the lower arm 104. At the same time, the lower jaw 110 pivots away from the upper jaw 116, thus opening the jaws 110, 116. The motion of the upper arm 102 relative to the lower arm 104 can also be described as a scissor motion. The upper arm 102 can be lowered to return the cutting forceps 100 to the closed position illustrated in FIG. 1A. As illustrated in FIG. 1B, in some embodiments, the upper arm 102 is also connected to a first end of a movement arm 160; the second end of the movement arm 160 is connected to an internal component of the lower arm body 112. Embodiments including the movement arm 160 are described in further detail below. In some embodiments the lower arm body 112 includes a switch arm slot 174 for receiving the switch arm 172. Embodiments including the switch arm 172 and switch arm slot 174 are described in further detail below.

Figure 2:
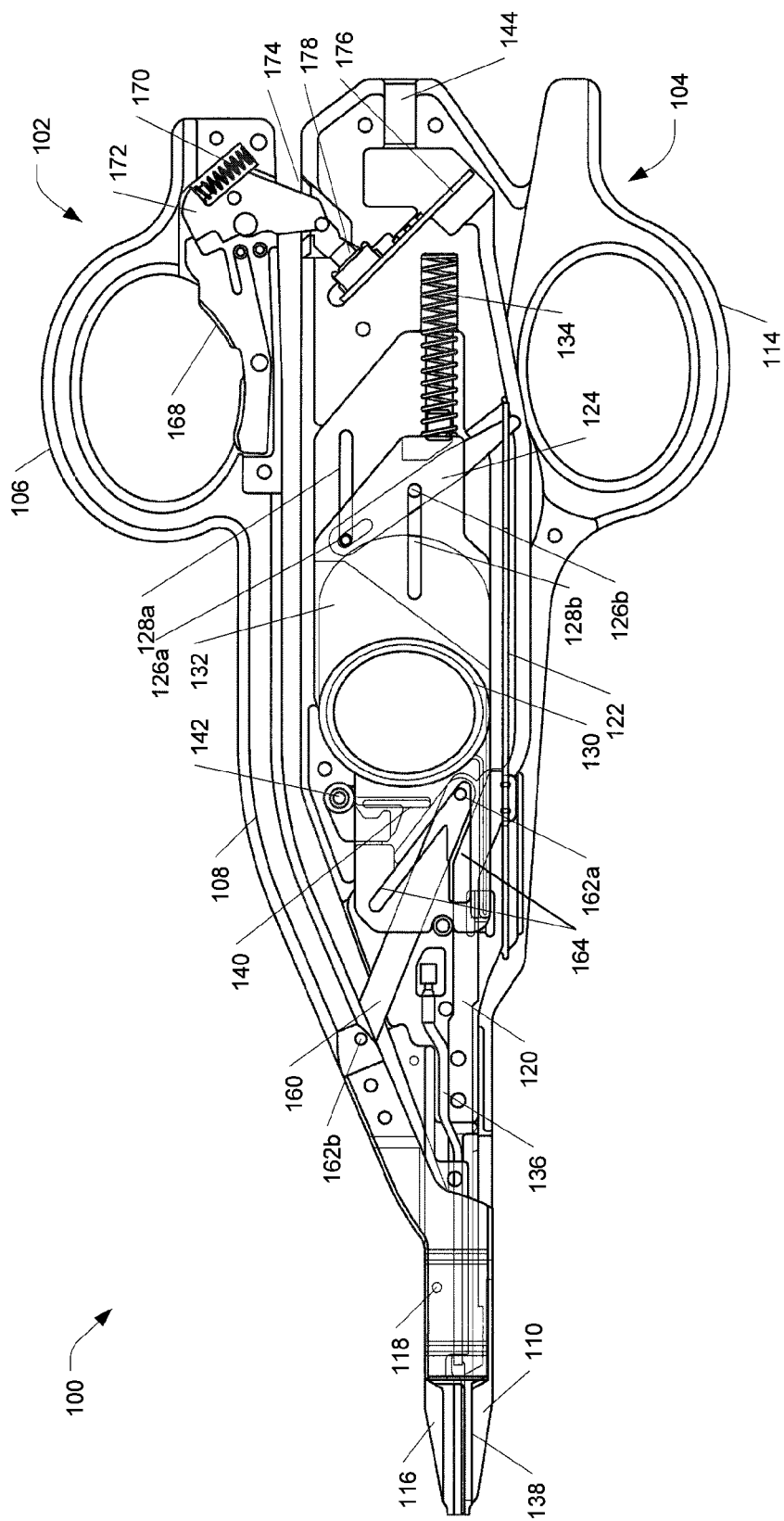
FIG. 2 illustrates a sideways transparent view of the cutting forceps shown in FIG. 1A.

FIG. 2 illustrates a sideways transparent view of the cutting forceps 100 shown in FIG. 1A. As illustrated in FIG. 2, the lower arm body 112 comprises a knife 120 and the mechanism for driving the knife 120, comprising a pull ring 130, a sliding or push plate 132, a return spring 134, a push arm 124, and a slide 122. The pull ring 130 provides the operator of the instrument control of the knife 120. The pull ring 130 is integrated into the push plate 132. The push plate 132 is mounted within the lower arm body 112 such that it is able to slide along the proximal-distal axis of the device. At its proximal side, the push plate 132 rests against the return spring 134. When the return spring 134 is in a relaxed or minimally compressed orientation, the push plate 132 is in a distal or neutral position; that is the pull ring 132 is further away from the operator of the device and the knife 120 is retracted. The push arm 124 is pivotally connected by two push arm pins 126a, 126b to a push plate 132. The push arm pins 126a, 126b are mounted within slots 128a, 128b in the lower arm body 112 and the push plate 132 such that the push arm pins 126a, 126b can slide within the slots 128a, 128b. The lower end of the push arm 124 rests against the proximal end of the slide 122. The distal end of the slide 122 is connected to the distal end of the knife 120. The proximal end of the knife 120 is positioned to translate distally between the upper 116 and lower 110 jaws. The operation of the knife 120 is further described below. In one embodiment, the push plate 132 may be replaced with a ring plate, without limitation.

FIG. 2 also illustrates the components of one embodiment of an RF sealing mechanism. The RF sealing mechanism comprises an electrode 136 that extends along the length of the jaws 110, 116 and into the lower arm body 112. Within the jaws 110, 116, the electrode 136 is partially surrounded by an insulator 138. In some embodiments, the electrode 136 is connected at its proximal end to an energy button circuit 140. The energy button circuit 140 is activated by the energy button 142, which activates the RF energy produced by the electrode 136. A port 144 in the proximal end of the lower arm body 112 is provided for connecting a cable (not shown) that provides an energy source to power the energy button circuit 140 and to generate the RF energy. The operation of the RF sealing mechanism is further described below.

FIG. 2 also illustrates the components of an embodiment of a knife lock out mechanism that may be included in some embodiments of the cutting forceps 100. The knife 120 lock out mechanism comprises the movement arm 160, an upper movement arm pin 162b, a lower movement arm pin 162a, and a slot 164 in the push plate 132. The operation of the lock out mechanism is described in further detail below.

FIG. 2 also illustrates the components of an embodiment of a trigger lock mechanism that may be included in some embodiments of the cutting forceps 100. The trigger lock mechanism comprises a lock button 168, a switch arm 172, a lock spring 170, a switch arm slot 174, a compression circuit 176, and a compression circuit button 178. The operation of the trigger lock mechanism is described in further detail below.

Figure 3:
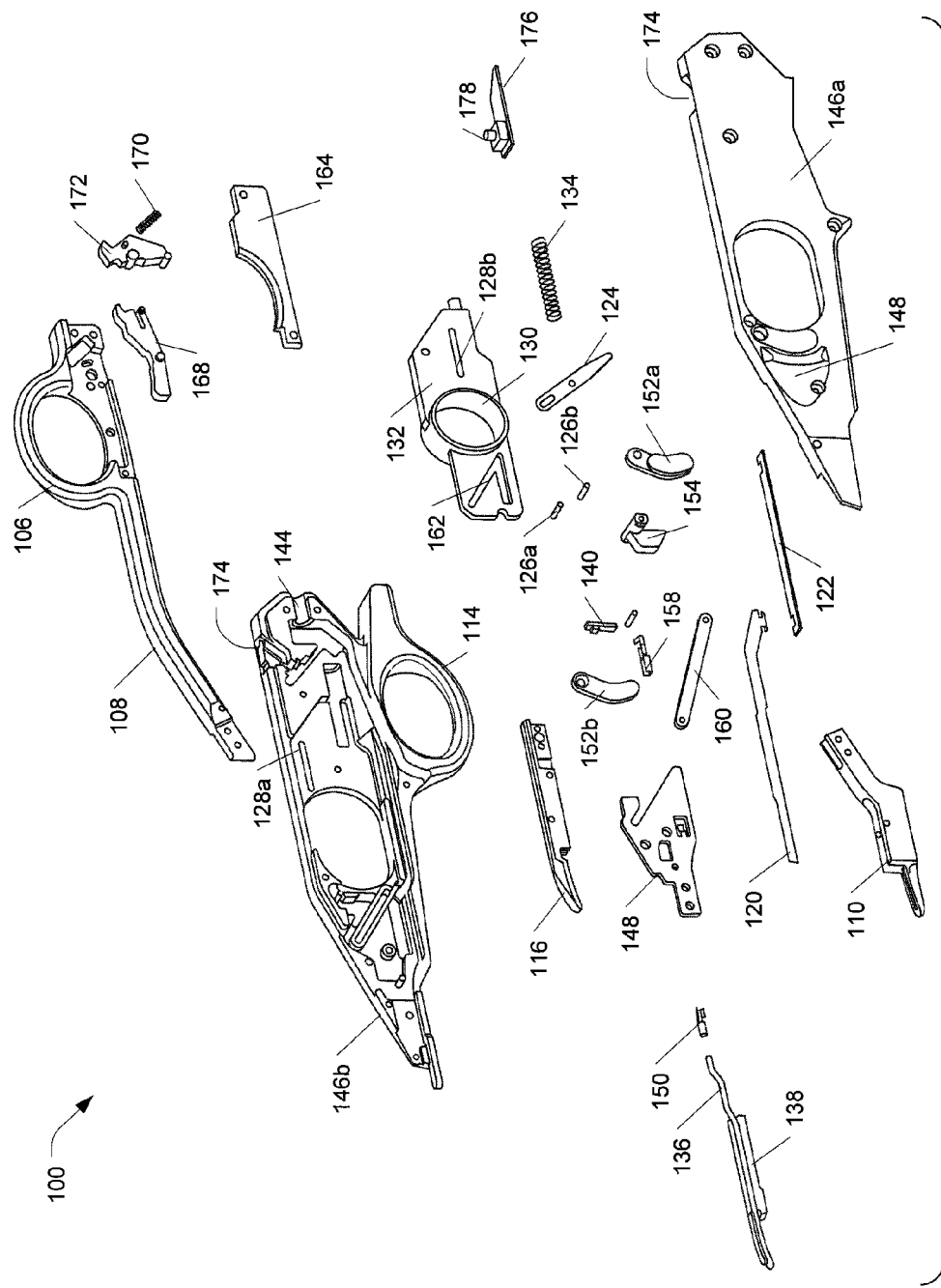
FIG. 3 illustrates an exploded view of the cutting forceps shown in FIG. 1A.

FIG. 3 illustrates an exploded view of the cutting forceps 100 shown in FIG. 1A. Illustrated are the constituent components of the cutting forceps 100, as well the components of various embodiments of the cutting forceps 100. The components of the cutting forceps 100 comprise an upper arm 102 and a lower arm 104, a cutting mechanism, and a sealing or coagulating mechanism.

The upper arm 102 comprises a bend arm 108 and an upper handle ring 106 integrally connected therewith. The upper arm 102 also comprises a lower jaw 110 configured to be connected to the distal end of the bend arm 108.

The lower arm 104 comprises an upper jaw 116. The upper jaw 116 is configured to be secured at its proximal end to an upper jaw tail 150. The upper jaw 116 comprises an electrode 136 that extends along the length of the upper jaw 116. The electrode 136 is partially surrounded by an insulator 138. The proximal end of the electrode 136 is coupled to an electrode connector 152. The electrode connector 152 connects the electrode 136 by means of wiring to the port 144 at the proximal end of the lower arm body 112 to receive power. The electrode connector 152 may also connect the electrode 136 to the energy button circuit 140. The energy button circuit 140 is connected to an energy button 142, shown here in exploded view as having a left 153a and a right 153 part, such that the energy button 142 can be operated from either the left or the right side of the cutting forceps 100. The energy button 142 also comprises a rocker 154 that is configured to allow the energy button 142 to pivot. A return connector 158 provides a connection to a return electrical path to the port 144.

The lower arm 104 also comprises a knife 120 for cutting tissue. The knife 120 is configured to connect at its proximal end to a slide 122, where the slide 122 is operable to push the knife 120 forwards (that is, towards the distal end of the cutting forceps 100) and retract the knife 120 backwards. The slide 122 is configured to connect at its proximal end to a push arm 124. The push arm 124 pivots on an upper push arm pin 126a and a lower push arm pin 126b. The upper push arm pin 126a rests within a slot 128a in the right lower arm body cover 146b. The lower push arm pin 126b rests within a slot 128b in a push plate 132. Both push arm pins 126a, 126b are configured to move within their respective slots 128a, 128b as the push plate 132 moves backwards (that is, towards the proximal end of the cutting forceps 100) and forwards. The push plate 132 comprises a pull ring 130 configured to receive a human finger. The push plate 132 rests against a return spring 134. The operating of the knife 120 is discussed in further detail below.

A left lower arm body cover 146a and a right lower arm body cover 146b enclose the knife 120 and its related parts, the electrode 136 and its related parts, and the upper jaw 116 and its related parts, except for the distal end of the upper jaw 116.

In some embodiments, the left lower arm body cover 146a and right lower arm body cover 146b also enclose a knife lock out mechanism. The knife lockout mechanism comprises a movement arm 160 and a slot 164 in the push plate 132. The knife lockout mechanism is described in further detail below.

In some embodiments, the cutting forceps 100 also comprises a trigger lock mechanism. The trigger lock mechanism comprises a lock button 168, a lock spring 170, and a switch arm 172 integrated with the upper handle ring 106 and fully or partially contained therein by an upper handle ring cover 166. The left 146a and right 146b lower body covers comprise a switch arm slot 174 for receiving the switch arm 172. Composed within the lower body 112 is a compression circuit 176 that comprises a compression circuit button 178. The trigger lock mechanism is described in further detail below.

Figure 4:
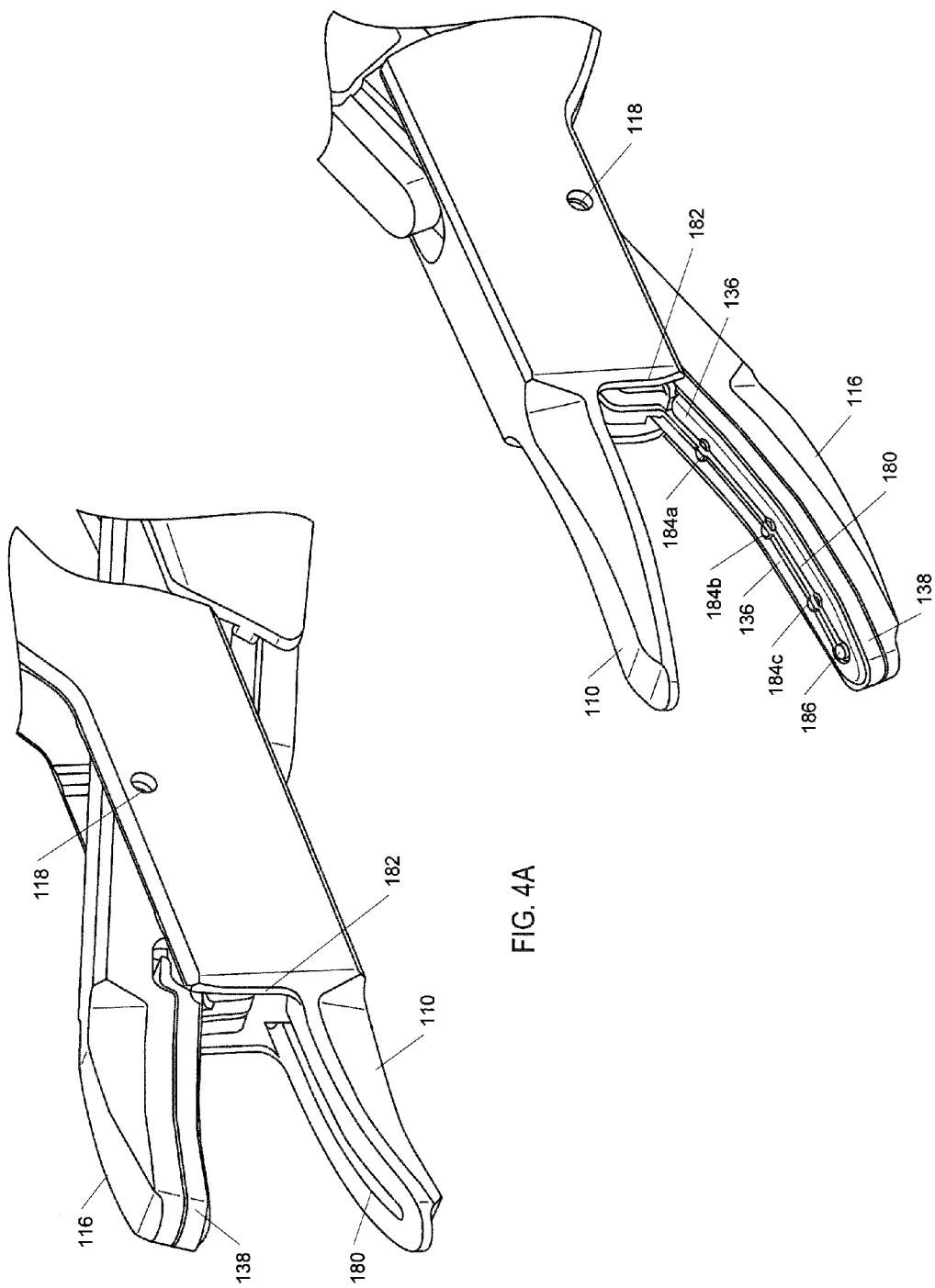
FIGS. 4A and 4B illustrate close up views of the jaws of the cutting forceps shown in FIG. 1A when the cutting forceps are in an open position.

FIGS. 4A and 4B illustrate close up views of the jaws 110, 116 of the cutting forceps 100 when the cutting forceps 100 shown in FIG. 1A are in an open position. FIG. 4A illustrates the cutting forceps 100 such that the first or lower jaw 110 is oriented downwards. The lower jaw 110 comprises a slot 180 configured so that a knife 120 housed within the lower arm 104 of the cutting forceps 100 can translate therein. The lower jaw 110 also comprises a tissue stop 182 configured to limit or block tissue within the jaws 110, 116 from advancing any further towards the proximal end of the jaws 110, 116. In some embodiments, the tissue-facing surface of the lower jaw 110 is smooth.

FIG. 4B illustrates the cutting forceps 100 such that the second or upper jaw 116 is oriented downwards and such that the tissue-facing surface of the upper jaw 116 is visible. The upper jaw 116 comprises an electrode 136 partially surrounded by an insulator 138. The electrode 136 extends from the interior of the lower arm body 112 along one side of the upper jaw 116 to the distal end of the upper jaw 116 and returns along the other side of the upper jaw 116, ending behind the tissue stop 182. The body of the electrode 136 thus forms a slot 180 within which the knife 120 can translate. Placed along the tissue-facing surface of the electrode 136 are one or more non-conductive teeth 184 configured to assist in gripping tissue placed between the jaws 110, 116. At the distal end of the upper jaw 116 is located an electrically conductive jaw stop 186 whose height above the tissue-facing surface of the upper jaw 116 sets the gap between the jaws 110, 116.

Figure 5:
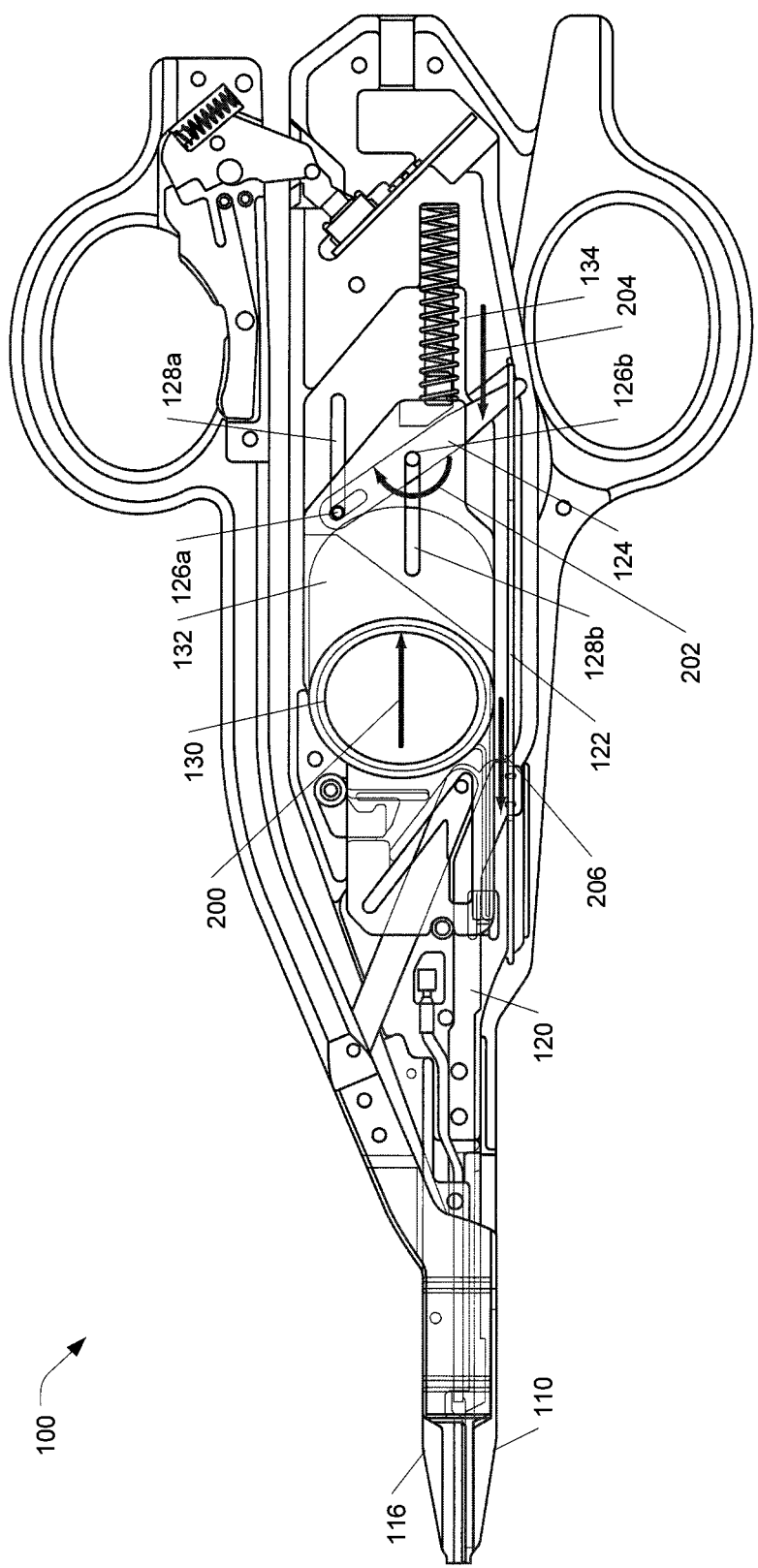
FIG. 5 illustrates a sideways transparent view of the cutting forceps shown in FIG. 1A, to illustrate the operation of the knife.

FIG. 5 illustrates a sideways transparent view of the cutting forceps 100 shown in FIG. 1A, to illustrate the operation of the knife 120. The knife 120 is configured to cut or sever tissue held between the jaws 110, 116 of the instrument. The knife mechanism comprises the knife 120, a slide 122, a push arm 124, a push plate 132, a pull ring 130 integrated into the push plate 132, and a return spring 134.

Operation of the knife 120 is initiated by drawing or pulling 200 the pull ring 130 in the proximal direction. As the push plate 132 moves in the proximal direction, it causes the push arm 124 to pivot 202, such that the upper or first end of the push arm 124 to moves proximally while the lower or second end of the push arm 124 moves distally. The distal motion of the lower end of the push arm 124 pushes 204 the slide 122 in a distal direction. The distal motion of the slide 122 pushes 206 the knife 120 in the distal direction, such that the knife translates distally between the jaws 110, 116.

As the push plate 132 is drawn 200, it applies pressure on and compresses the return spring 134. Once the operator releases the pull ring 130, the return spring 134 pushes the push plate 132 in a distal direction and back into the neutral position. The distal motion of the push plate 132 reverses the movement of the push arm 124, the slide 122, and the knife 120, thus retracting the knife 120 from the jaws 110, 116.

Figure 6:
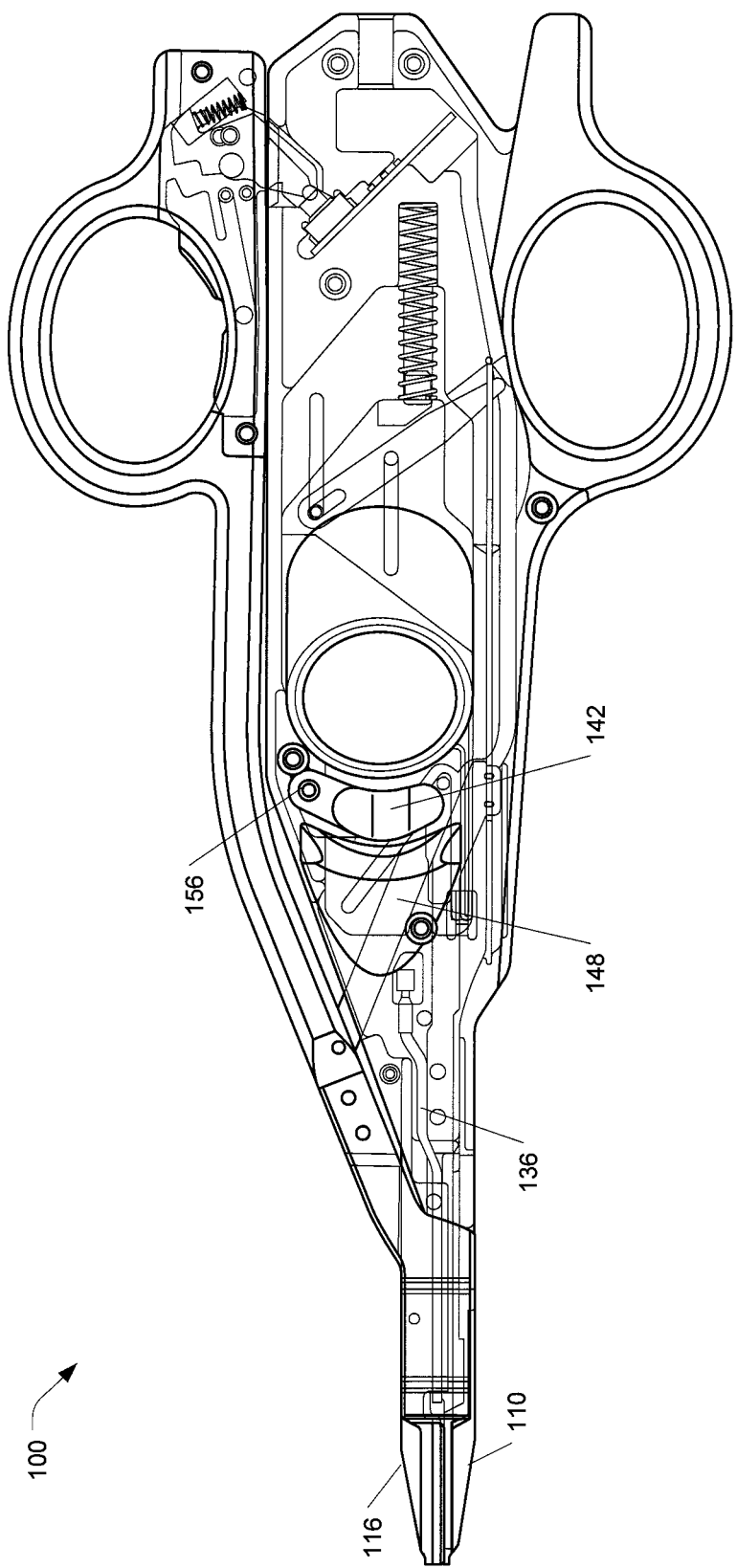
FIG. 6 illustrates a sideways partially transparent view of the cutting forceps shown in FIG. 1A to illustrate the operation of the RF sealing mechanism.

FIG. 6 illustrates a sideways partially transparent view of the cutting forceps 100 shown in FIG. 1A to illustrate the operation of the RF sealing mechanism. RF energy may be used to seal or coagulate tissue held between the jaws 110, 116 of the cutting forceps 100. The RF sealing mechanism comprises an energy button 142, an energy button circuit (not visible), and an electrode 136. The RF energy is activated by the energy button 142, which is configured to rotate around a pivot 156. A bump 148 on the exterior of the instrument prevents inadvertent activation of the energy button 142. Rotation of the energy button 142 informs the energy button circuit to activate the RF energy. RF energy is delivered by the electrode 136 to the jaws 110, 116 of the cutting forceps 100. Releasing the energy button 142 stops delivery of RF energy by the electrode 136.

The knife mechanism described with respect to FIG. 5 and the RF sealing mechanism described with respect to FIG. 6 can be used separately or together. That is, the operator of the instrument can choose to activate the knife without also activating the RF energy. Similarly, the operator can choose to activate the RF energy without also activating the knife. The operator can also choose to seal and cut, typically in that order, by activating the RF energy and subsequently activating the knife.

Knife Lockout

Safe and effective operation of the knife, as described above, may raise at least two concerns that may be addressed by a knife lockout mechanism. First, it may be desirable to prevent the knife from firing until the jaws are sufficiently closed to cut the tissue held by the jaws. Second, it may be desirable to prevent the jaws from opening until the knife has been retracted. The first safety concern seeks to prevent the jaws from being wider apart than the knife is tall, so that the knife will always cut through all layers of the tissue held by the jaws. The second safety concern seeks to prevent the knife from being exposed and inadvertently cutting tissue that was not meant to be cut.

FIG. 7 illustrates a sideways transparent view of one embodiment of a cutting forceps 1100 that comprises a knife lockout mechanism. The cutting forceps 1100 is similar to the cutting forceps 100 of FIGS. 1-6. As illustrated in FIG. 7, the cutting forceps 1100 comprises an upper arm 1102 pivotally connected to a lower arm 1104 at a pivot joint 1118. The upper arm 1102 is connected to a lower jaw 1110 and comprises an upper handle ring 1106 shaped such that a human finger can be inserted therein. The lower arm 1104 comprises a lower arm body 1112, a lower handle ring 1114, and an upper jaw 1116. The lower arm body 1112 comprises an electrode 1136 for supplying RF energy, wherein the electrode 1136 extends from the lower arm body 1112 along the length of the jaws 1110, 1116. The lower arm body 1112 also comprises a knife 1120 that is connected to a slide 1122. The slide 1122 is pushed and pulled at its proximal end by a push arm 1124. The push arm 1124 is pivotally connected to a push plate 1132. The push plate 1132 comprises a pull ring 1130, wherein the pull ring 1130 is shaped to accept a human finger. The proximal side of the push plate 1132 rests against a return spring 1134 that is operable to return the push plate 1132 to a neutral position from a drawn position.

The cutting forceps 1100 also comprises a knife lockout mechanism. The knife lockout mechanism comprises a movement arm 1160 and a slot 1164. The movement arm 1160 provides a link between the upper arm 1102 of the cutting forceps 1100 and the knife firing mechanism, that is, the pull ring 1130 and the push plate 1132. The lower or second end of the movement arm 1160 is connected to a lower movement arm pin 1162a. The lower movement arm pin 1162a rides in the slot 1164. The slot 1164 is cut into the push plate 1132 and thus moves in tandem with the push plate 1132 as the push plate 1132 causes the knife 1120 to be fired and retracted. The upper or first end of the movement arm 1160 is pivotally connected to the upper arm 1102 of the cutting forceps 1100 by way of an upper movement arm pin 1162b.

FIG. 7 illustrates the cutting forceps 1100 in an open position, that is, with the jaws 1110, 1116 fully parted. In this position, the lower movement arm pin 1162a rests at the top of the slot 1164. The slot 1164 is shaped such that the lower movement arm pin 1162a prevents the push plate 1132 from moving until the jaws 1110, 1116 are partially or entirely closed.

FIG. 8 illustrates a close-up transparent view of the knife lockout mechanism of the cutting forceps shown in FIG. 7. As illustrated by FIG. 8, the slot 1164 is cut into the push plate 1132. The lower movement arm pin 1162a rides in the slot 1164. When the cutting forceps 1100 are in the fully open position, the lower movement arm pin 1162a rests at one end of the slot 1164.

In some embodiments, the slot 1164 comprises an angled "L" shape such that upper or upright arm portion of the slot is at an angle to the direction of travel of the push plate 1132 and the lower or horizontal portion of the slot 1164 is parallel to the direction of travel of the push plate 1132. In such embodiments, the angle of the upright portion of the slot 1164 and the location of the lower movement arm pin 1162a within the upright portion of the slot 1164 prevents the push plate 1132 from moving forwards or backwards. The lower movement arm pin 1162a must travel to the horizontal portion of the slot 1164 in order for the push plate 1132 to be able to move. The horizontal portion of the slot 1164 is positioned parallel to the direction of travel of the push plate 1132. The position of lower movement arm pin 1162a within the horizontal portion of the slot 1164 thus operates to prevent the cutting forceps 1100 from being opened. The push plate 1132 must be returned to the neutral position such that the lower movement arm pin 1162a can access the upright portion of the slot 1164 before the cutting forceps 1100 can be opened.

In some embodiments, the slot 1164 comprises a vertical shape (not shown) such that the body of slot is perpendicular to the direction of travel of the push plate 1132. In such embodiments, the slot 1164 causes the movement of the upper arm 1102 and the push plate 1132 to be proportional, such that as the upper arm 1102 moves up (that, is into the open position) the push plate 1132 moves towards the distal end of the instrument, into the neutral position. Similarly, as the upper arm 1102 moves down (that is, into the closed position), the push plate 1132 moves towards the proximal end of the instrument and may cause the knife 1120 to be extended.

Figure 9:
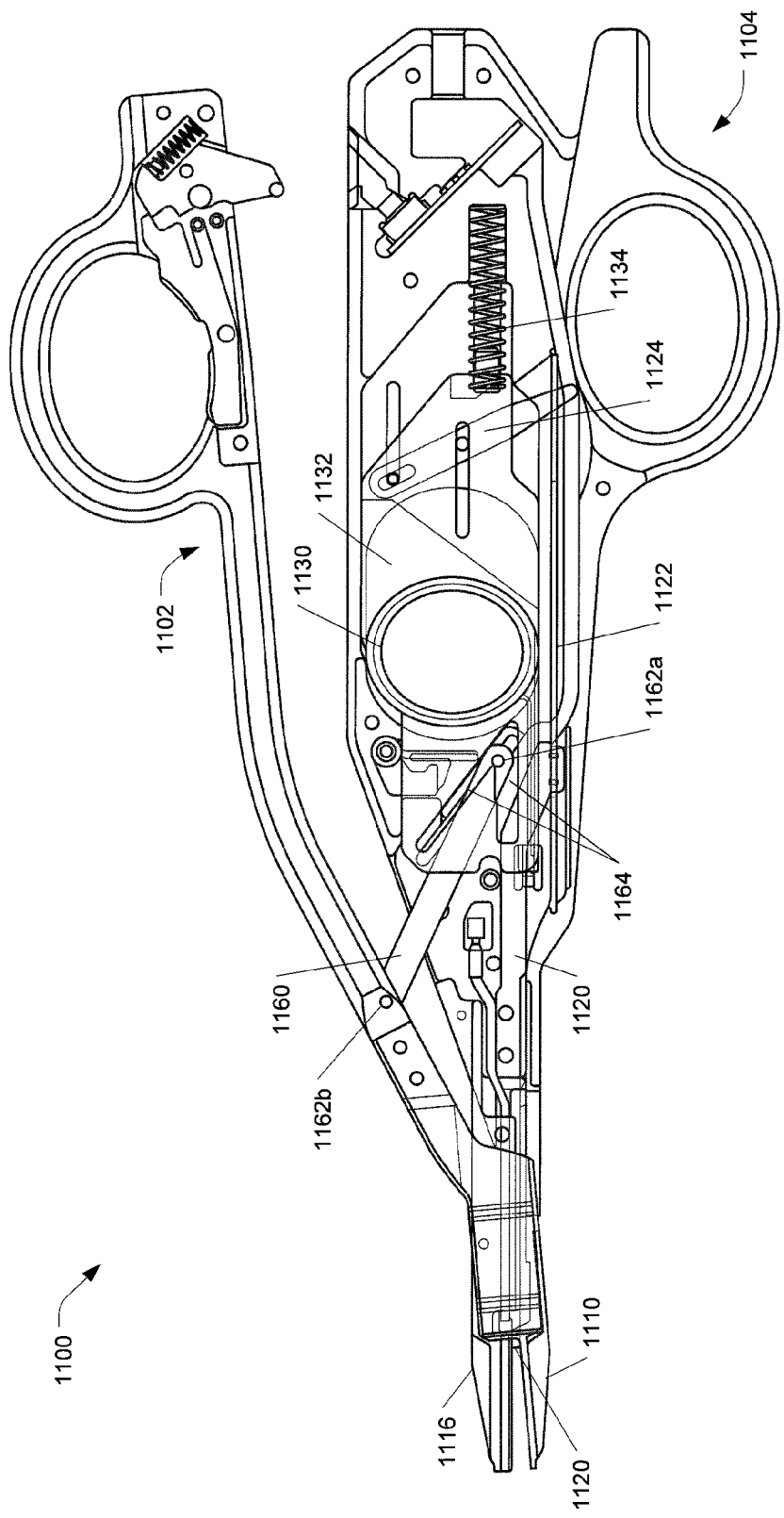
FIG. 9 illustrates a sideways transparent view of the cutting forceps shown in FIG. 7 with an angled "L" shape slot 1164 and in a partially closed position.

FIG. 9 illustrates a sideways transparent view of the cutting forceps 1100 shown in FIG. 7 with an angled "L" shape slot 1164 and in a partially closed position. As the upper arm 1102 moves towards the closed position, it drives the movement arm 1160 such that the movement arm 1160 pivots at the upper movement arm pin 1162b. The lower movement arm pin 1162a rides along the upper or upright portion of the slot 1164 until the lower movement arm pin 1162a reaches the lower or horizontal portion of the slot 1164. Near the top of the horizontal portion of the slot 1164 there may be some play between the lower movement arm pin 1162a and the slot 1164 such that the push plate 1132 can move; however, the knife 1130 will only be able to advance slightly, and not far enough to cut any tissue, due to the lower movement arm pin 1162 being blocked by the edge of the slot 1164. The lower movement arm pin 1162a may reach the horizontal portion of the slot 1164 when the jaws 1110, 1116 are partially closed, such as for instance at five degrees relative to each other. Once the lower movement arm pin 1162a reaches the horizontal portion of the slot 1164, the push plate 1132 may be free to move.

Figure 10:
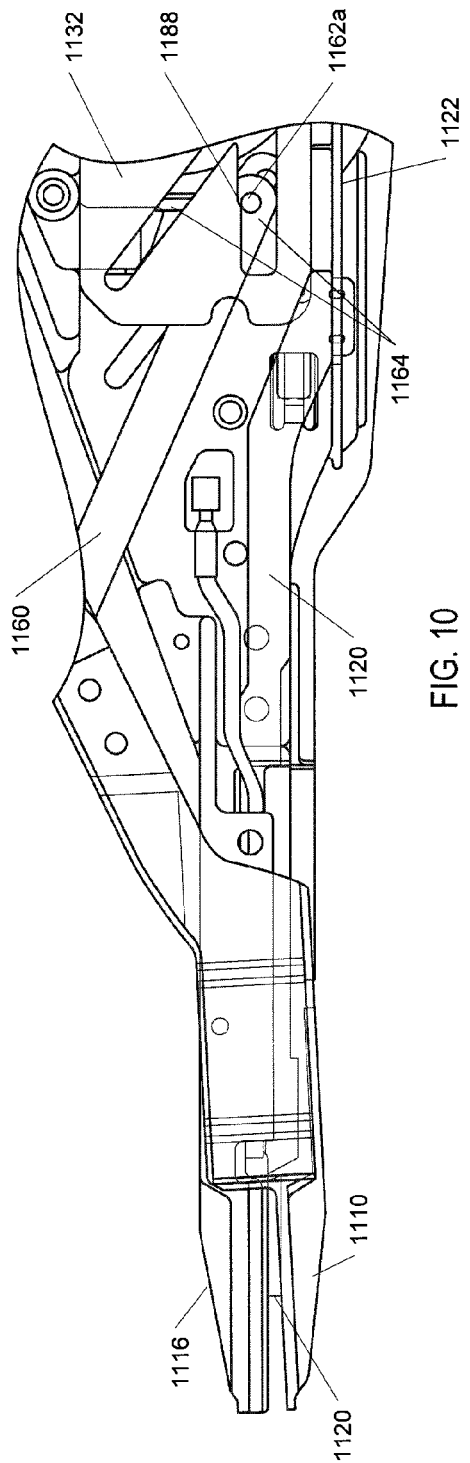
FIG. 10 illustrates a close up transparent view of the distal end of one embodiment of the cutting forceps shown in FIG. 7 where the knife can be partially drawn.

In some embodiments, the slot 1164 is shaped such that the knife 1120 can be partially drawn when the jaws 1110, 1116 are partially closed. FIG. 10 illustrates a close up transparent view of the distal end of one such embodiment of the cutting forceps 1100 shown in FIG. 7. In the embodiment of FIG. 10, the slot 1164 comprises a first stop 1188. The first stop 1188 prevents the push plate 1132 from being drawn past a certain distance, thus allowing the knife 1120 to only advance a partial distance along the jaws 1110, 1116. This allows for partial cutting of tissue. For example, when the jaws 1110, 1116 are at five degrees relative to each other, the first stop 1188 may be positioned such that the knife 1120 can advance 0.07 inches from the initial cutting position. The slot 1164 may comprise additional stops; for instance, at three degrees between the jaws 1110, 1116, the knife 1120 may be able to advance 0.3 inches from the initial cutting position. After the final stop, the knife 1120 is able to complete a full stroke. For example, at two to zero degrees between the jaws, the knife 1120 can advance along the entire length of the jaws 1110, 1116.

Figure 11:
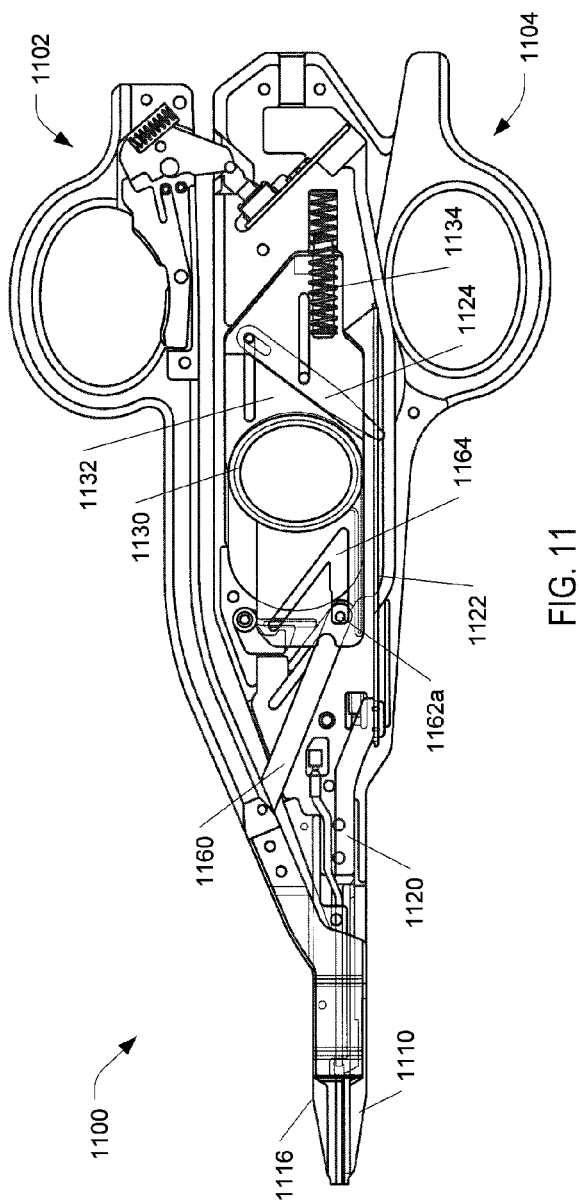
FIG. 11 illustrates a sideways transparent view of the cutting forceps shown in FIG. 7 in a fully closed position, with the knife fully advanced.

FIG. 11 illustrates a sideways transparent view of the cutting forceps 1100 shown in FIG. 7 in a fully closed position, with the knife 1120 fully advanced. When the cutting forceps 1100 are in the fully closed position, the lower movement arm pin 1162a has full access to the horizontal portion of the slot 1164, and the push plate 1132 is free to be pulled to its full extent. In this position, the push plate 1132 is fully drawn and the knife 1120 is fully advanced. The position of the lower movement arm pin 1162a in the horizontal portion of the slot 1164 prevents the cutting forceps 1100 from being opened while the knife 1120 is extended. Once the push plate 1132 is returned to the neutral position, thus retracting the knife 1120, the lower movement arm pin 1162a can once again travel up the upper portion of the slot 1164, allowing the cutting forceps 1100 to be opened.

Figure 12:
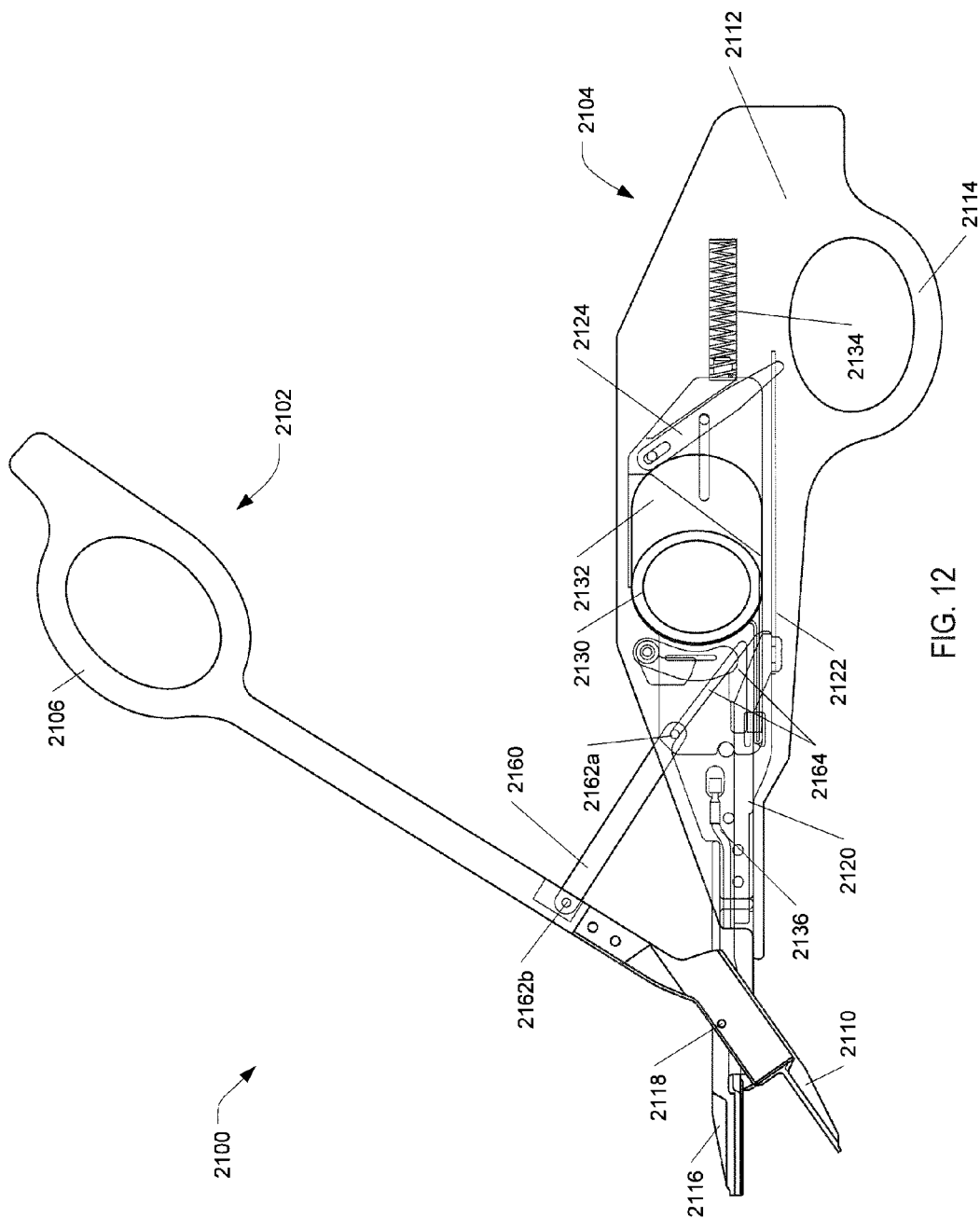
FIG. 12 illustrates sideways transparent view of an embodiment of a cutting forceps with a knife lockout mechanism, in a fully open position.

FIG. 12 illustrates sideways transparent view of one embodiment of a cutting forceps 2100 with a knife lockout mechanism, in a fully open position. The cutting forceps 2100 is similar to the cutting forceps 100 of FIGS. 1-6. As illustrated in FIG. 12, the cutting forceps 2100 comprises an upper arm 2102 pivotally connected to a lower arm 2104 at a pivot joint 2118. The upper arm 2102 is connected to a lower jaw 2110 and comprises an upper handle ring 2106 shaped such that a human finger can be inserted therein. The lower arm 2104 comprises a lower arm body 2112, a lower handle ring 2114, and an upper jaw 2116. The lower arm body 2112 comprises an electrode 2136 for supplying RF energy, wherein the electrode 2136 extends from the lower arm body 2112 along the length of the jaws 2110, 2116. The lower arm body 2112 also comprises a knife 2120 that is connected to a slide 2122. The slide 2122 is pushed and pulled at its proximal end by a push arm 2124. The push arm 2124 is pivotally connected to a push plate 2132. The push plate 2132 comprises a pull ring 2130, wherein the pull ring 2130 is shaped to accept a human finger. The proximal side of the push plate 2132 rests against a return spring 2134 that is operable to return the push plate 2132 to a neutral position from a drawn position.

The cutting forceps 2100 also comprises a knife lockout mechanism. The knife lockout mechanism comprises a movement arm 2160 and a slot 2164. The movement arm 2160 provides a link between the upper arm 2102 of the cutting forceps 2100 and the knife firing mechanism, that is, the pull ring 2130 and the push plate 2132. The lower or second end of the movement arm 2160 is connected to a lower movement arm pin 2162a. The lower movement arm pin 2162a rides in the slot 2164. The slot 2164 is cut into the push plate 2132 and thus moves in tandem with the push plate 2132 as the push plate 2132 causes the knife 2120 to be fired and retracted. The upper or first end of the movement arm 2160 is pivotally connected to the upper arm 2102 of the cutting forceps 2100 by way of an upper movement arm pin 2162b.

FIG. 12 illustrates the cutting forceps 2100 in an open position, that is, with the jaws 2110, 2116 fully parted. In this position, the lower movement arm pin 2162a rests at one end of the slot 2164.

Figure 13:
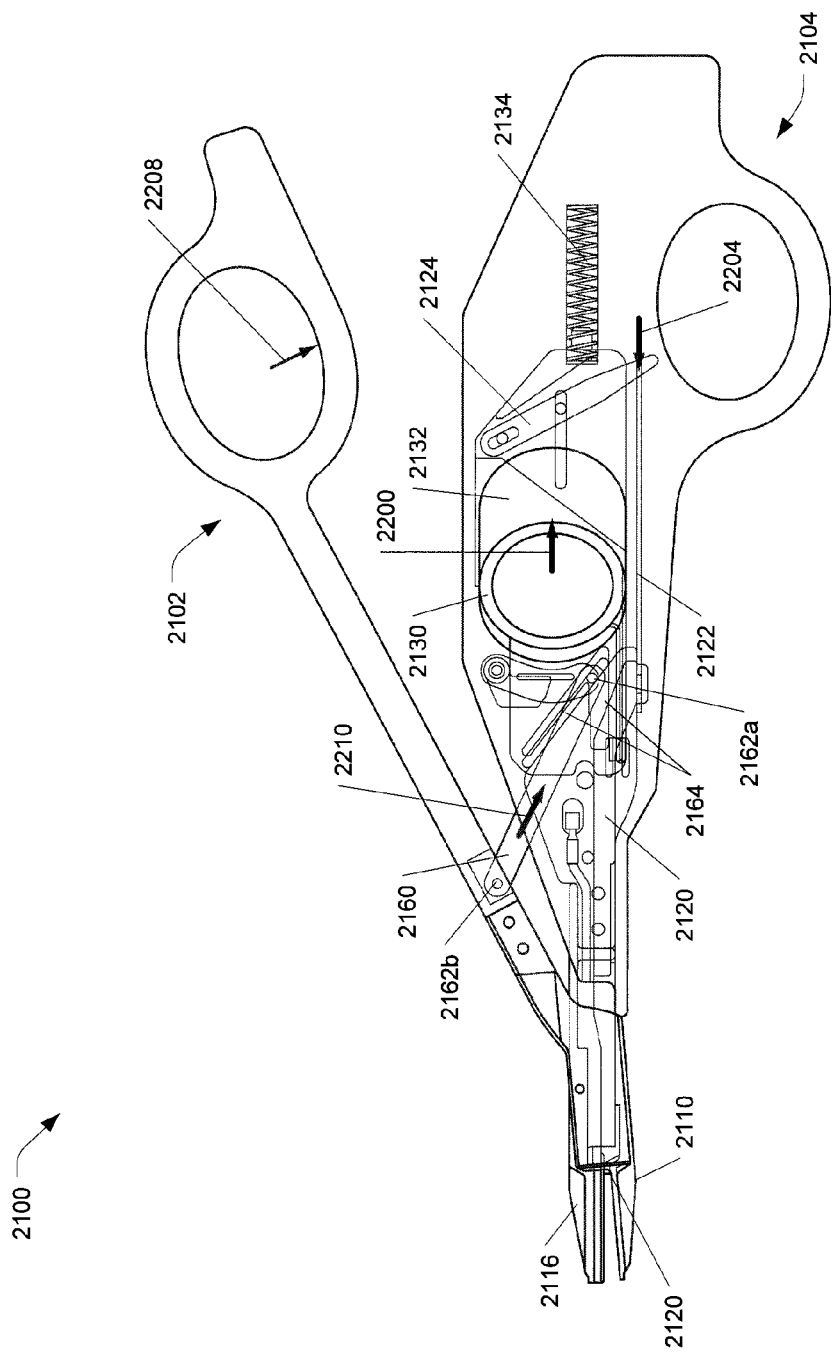
FIG. 13 illustrates a sideways transparent view of the cutting forceps shown in FIG. 12 in a partially closed position.

FIG. 13 illustrates a sideways transparent view of the cutting forceps 2100 shown in FIG. 12 in a partially closed position. As the upper arm 2102 moves 2208 towards the closed position, it drives 2210 the movement arm 2160 such that the movement arm 2160 pivots at the upper movement arm pin 2162b. The lower movement arm pin 2162a rides along the upper or upright portion of the slot 2164. The lower movement arm pin 2162a may reach the lower or horizontal portion of the slot 2164 when the jaws 2110, 2116 are partially closed, such as for instance at five degrees relative to each other. Once the lower movement arm pin 2162a reaches the horizontal portion of the slot 2164, the push plate 2132 may be free to be drawn 2200. When the push plate 2132 is drawn 2200 in the proximal direction, it causes the push arm 2124 to push 2204 the slide 2122, as described above.

Figure 14:
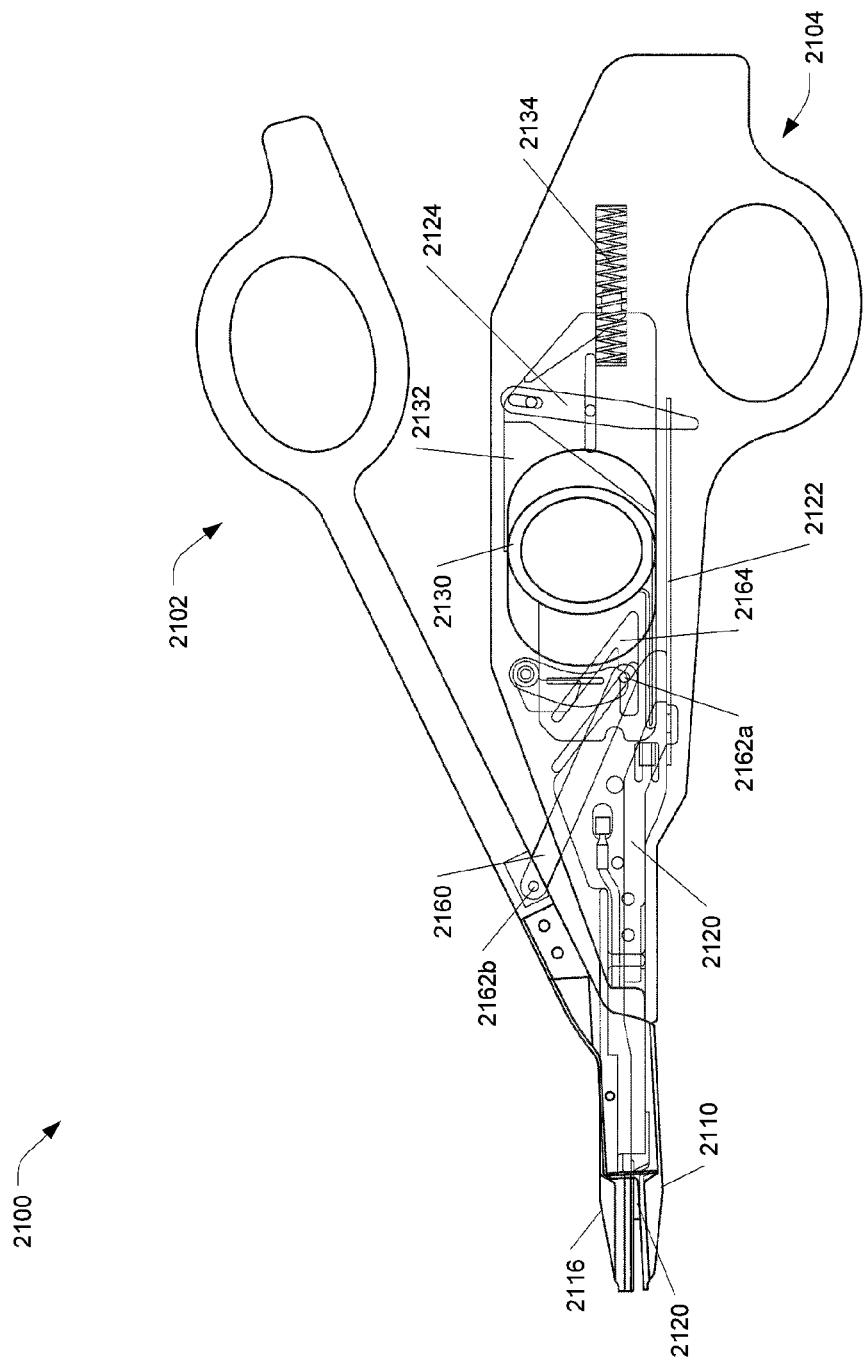
FIG. 14 illustrates a sideways transparent view of the cutting forceps shown in FIG. 12 in a nearly closed position.

In some embodiments, the slot 2164 is shaped such that the knife 2120 can be partially drawn when the jaws 2110, 2116 are partially closed. FIG. 14 illustrates a sideways transparent view of the cutting forceps 2100 shown in FIG. 12 in a nearly closed position. In some embodiments, the slot 2164 may comprise a first stop. The first stop prevents the push plate 2132 from being drawn past a certain distance, thus allowing the knife 2120 to only advance a partial distance along the jaws 2110, 2116. This allows for partial cutting of tissue. For example, when the jaws 2110, 2116 are at five degrees relative to each other, the first stop may be positioned such that the knife 2120 can advance 0.07 inches from the initial cutting position. The slot 2164 may comprise additional stops; for instance, at three degrees between the jaws 2110, 2116, the knife 2120 may be able to advance 0.3 inches from the initial cutting position. After the final stop, the knife 2120 is able to complete a full stroke. For example, at two to zero degrees between the jaws, the knife 2120 can advance along the entire length of the jaws 2110, 2116.

Figure 15:
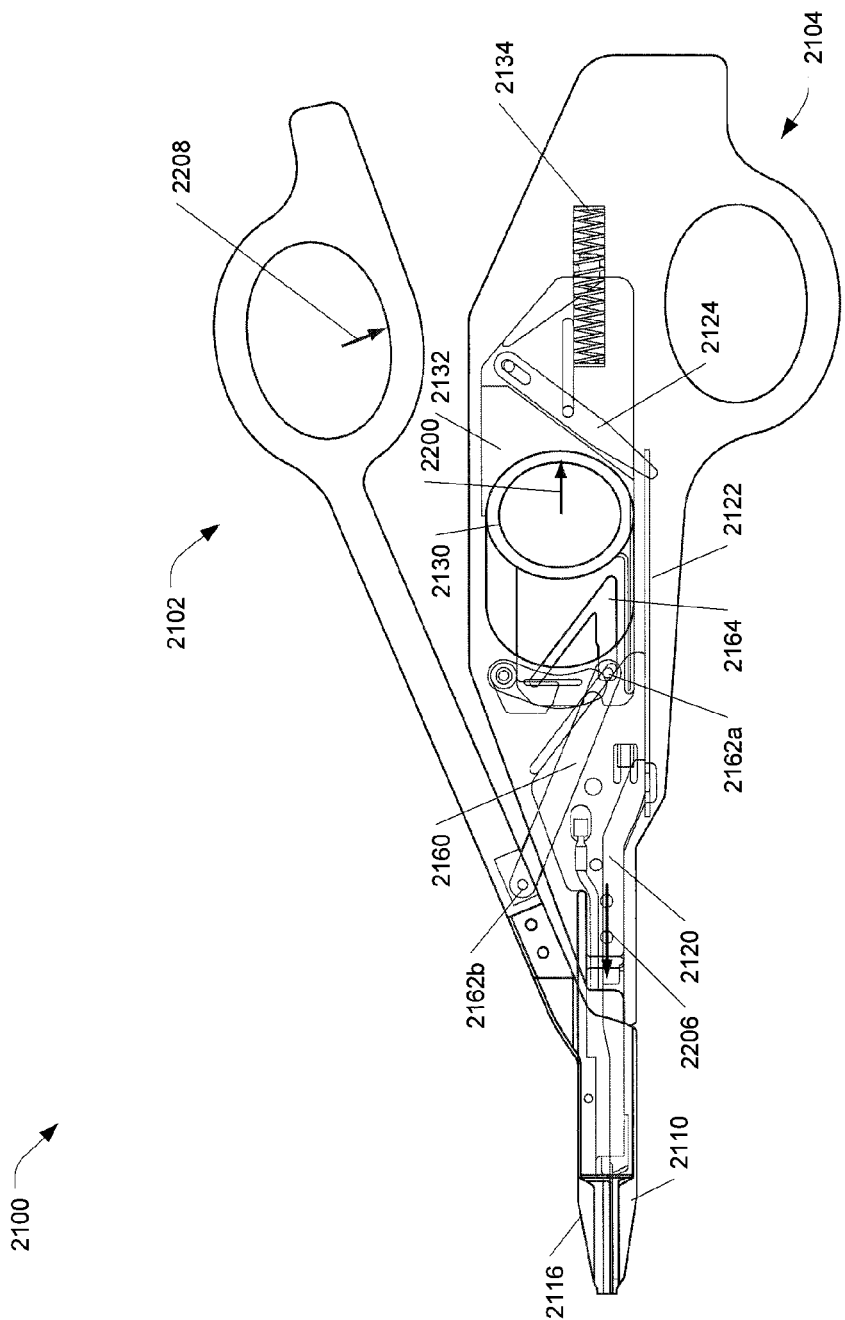
FIG. 15 illustrates a sideways transparent view of the cutting forceps shown in FIG. 12 in a fully closed position, with the knife fully advanced.

FIG. 15 illustrates a sideways transparent view of the cutting forceps 2100 shown in FIG. 12 in a fully closed position, with the knife 2120 fully advanced. When the cutting forceps 2100 are in the fully closed position, the lower movement arm pin 2162a has full access to the horizontal portion of the slot 2164, and the push plate 2132 is free to move to its full extent. In this position, the push plate 2132 is fully drawn 2200 and the knife 2120 is fully advanced 2206. The position of the lower movement arm pin 2162a in the horizontal portion of the slot 2164 prevents the cutting forceps 2100 from being opened while the knife 2120 is extended. Once the push plate 2132 has returned to the neutral position, thus retracting the knife 2120, the lower movement arm pin 2162a can once again travel up the upper portion of the slot 2164, allowing the cutting forceps 2100 to be opened.

Trigger Lockout

When using a cutting forceps as described above, it may be desirable to lock the jaws shut on tissue. This allows the operator to remove his or her hands from the device and use the cutting forceps similar to a surgical clamp. The cutting forceps should only lock when desired and not automatically.

The RF energy that seals or coagulates tissue should also only be activated at the desired time. Specifically, it may be desirable to activate the RF energy only when there is sufficient pressure on the jaws of the device. This typically occurs when the forceps arms are fully closed and one arm is possibly flexing to provide a load on the distal ends of the jaws. Thus it is desirable that the RF energy activation be disabled unless the jaws are fully closed. It is also desirable, however, for the operator to be able to close the jaws of the device without activating the RF energy.

Figure 16:
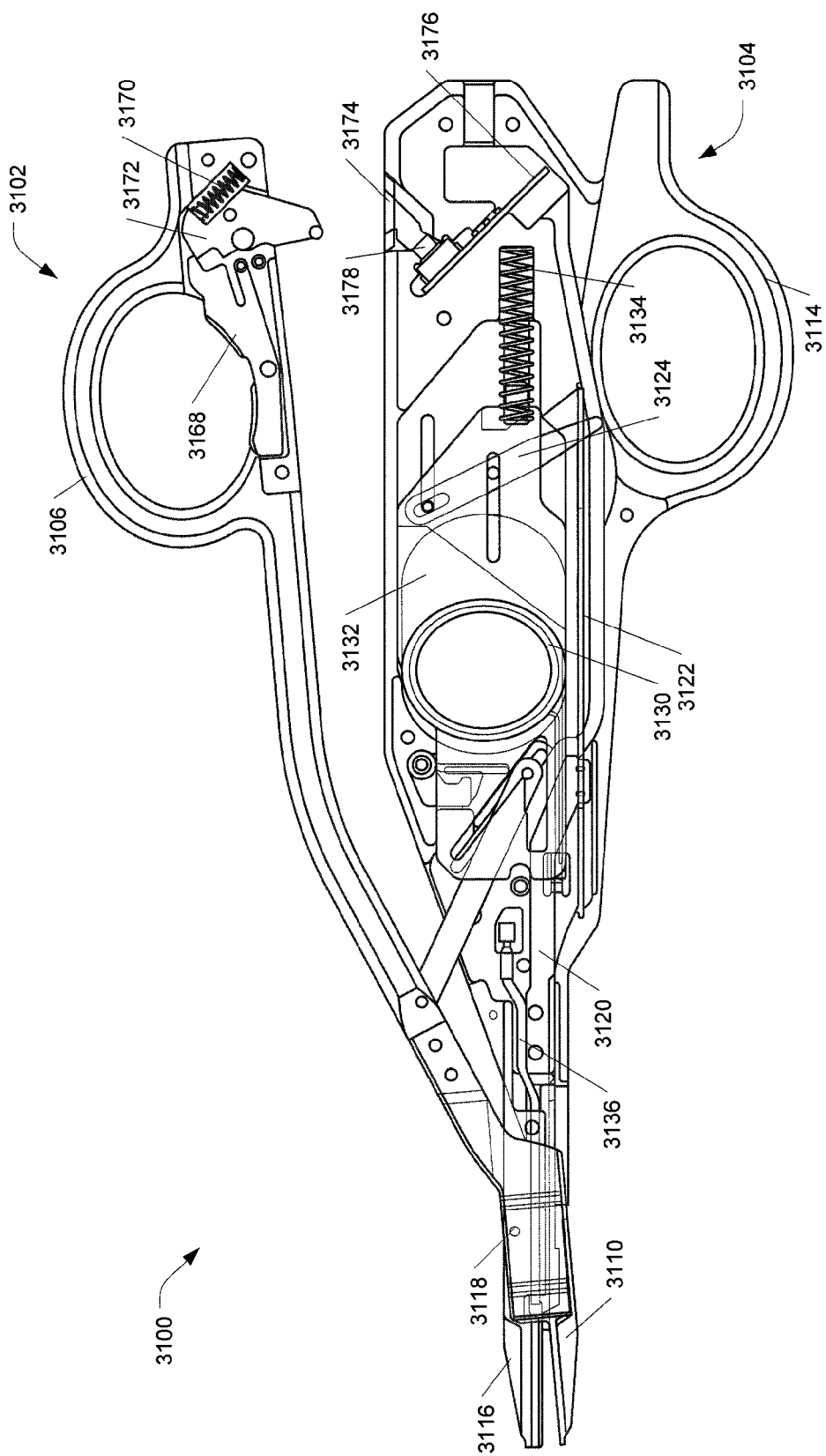
FIG. 16 illustrates a sideways transparent view of one embodiment of a cutting forceps with a trigger lockout mechanism.

FIG. 16 illustrates a sideways transparent view of one embodiment of a cutting forceps 3100 with a trigger lockout mechanism. The cutting forceps 3100 is similar to the cutting forceps 100 of FIGS. 1-6. As illustrated in FIG. 7, the cutting forceps 3100 comprises an upper arm 3102 pivotally connected to a lower arm 3104 at a pivot joint 3118. The upper arm 3102 is connected to a lower jaw 3110 and comprises an upper handle ring 3106 shaped such that a human finger can be inserted therein. The lower arm 3104 comprises a lower arm body, a lower handle ring 3114, and an upper jaw 3116. The lower arm body comprises an electrode 3136 for supplying RF energy, wherein the electrode 3136 extends from the lower arm body along the length of the jaws 3110, 3116. The lower arm body also comprises a knife 3120 that is connected to a slide 3122. The slide 3122 is pushed and pulled at its proximal end by a push arm 3124. The push arm 3124 is pivotally connected to a push plate 3132. The push plate 3132 comprises a pull ring 3130, wherein the pull ring 3130 is shaped to accept a human finger. The proximal side of the push plate 3132 rests against a return spring 3134 that is operable to return the push plate 3132 to a neutral position from a drawn position.

The cutting forceps 3100 also comprises a trigger lockout mechanism. The trigger lockout mechanism comprises a lock button 3168, a lock spring 3170, a switch arm 3172, and a switch arm slot 3174. The lock button 3168 is integrated into the upper handle ring 3106 such that it can be accessed by a human finger inserted into the upper handle ring 3106. The switch arm 3172 is rotatably mounted in the upper arm 3102 and comprises a first end that extends from the upper arm 3102 underneath the upper handle ring 3106 and towards the lower arm 3104. The switch arm 3172 also comprises a second end that rests against the lock spring 3170. The switch arm slot 3174 is located in the lower arm 3104 such that the first end of the switch arm 3172 will pass into the switch arm slot 3174 when the forceps arms 3102, 3104 are closed.

Figure 17:
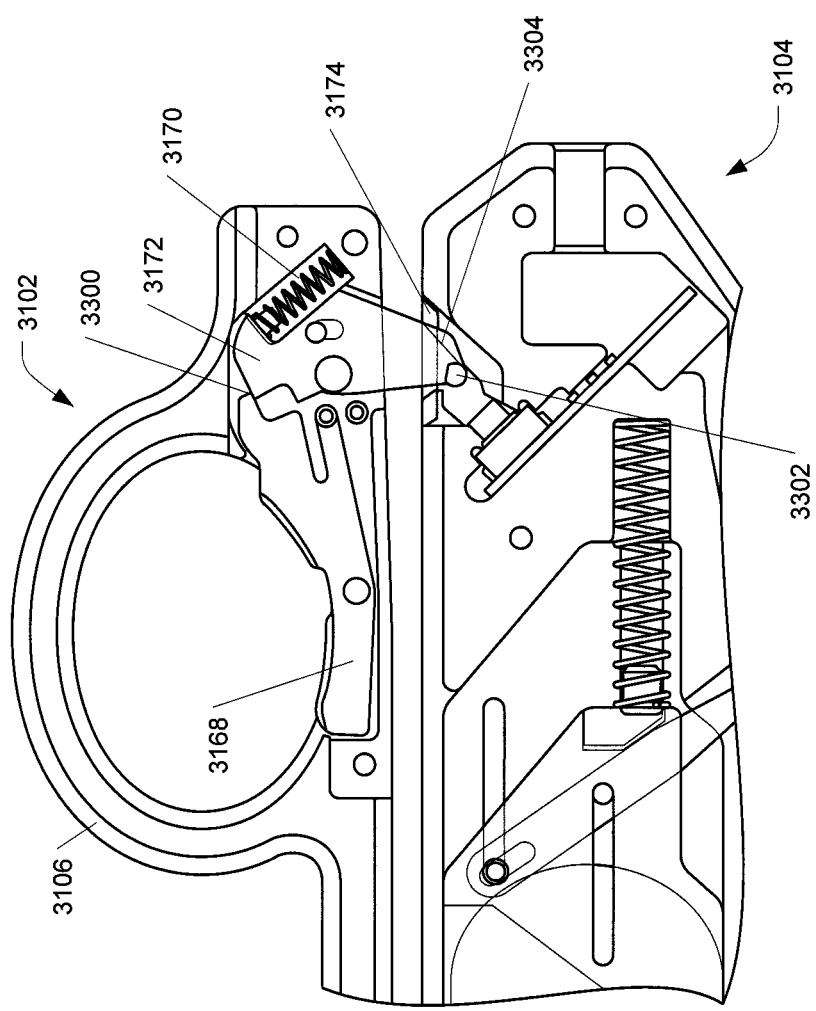
FIG. 17 illustrates a close-up transparent view of a portion of the proximal end of the cutting forceps shown in FIG. 16.

FIG. 17 illustrates a close-up transparent view of a portion of the proximal end of the cutting forceps 3100 shown in FIG. 16. Illustrated is the neutral position of the switch arm 3172, in which is the lock spring 3170 is relaxed or minimally compressed and the switch arm 3172 is positioned to enter and exit the switch arm slot 3174 with ease. Also illustrated is a first position of the lock button 3168. In this position, the lock button 3168 makes contact with the switch arm 3172 at a first contact point 3300 at the proximal end of the lock button 3168. The first contact point 3300 is such that the switch arm 3172 prevents the lock button 3168 from moving, effectively locking the lock button 3168 in the first position.

FIG. 17 also illustrates the point at which the upper 3102 and lower 3104 arms of the cutting forceps 3100 shown in FIG. 16 have initially been closed, such that the switch arm 3172 has entered the switch arm slot 3174. As the switch arm 3172 enters the switch arm slot 3174, a protrusion 3302 on the end of the switch arm 3172 makes contact with a ramp or guide or slot path 3304 in the switch arm slot 3174.

Figure 18:
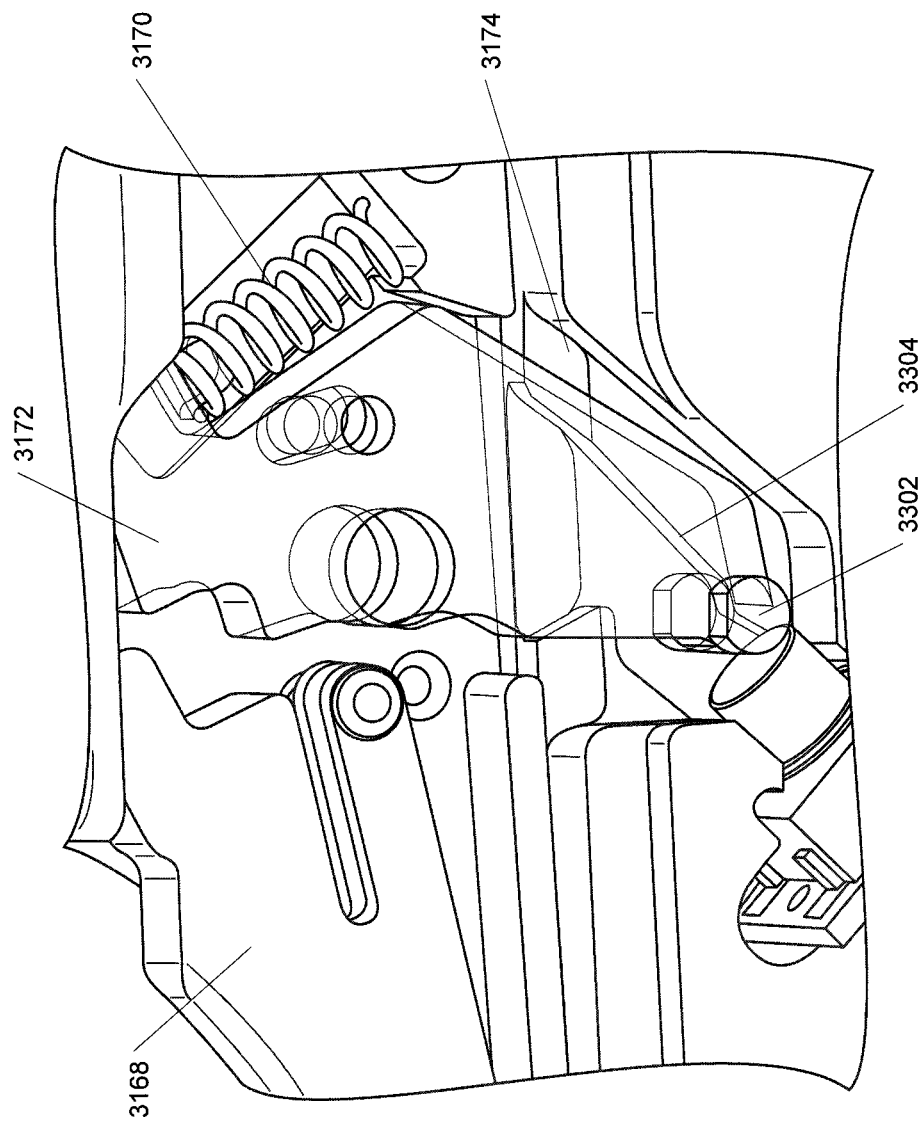
FIG. 18 illustrates a close-up transparent angled view of one embodiment of the switch arm in the switch arm slot of the cutting forceps shown in FIG. 16.

FIG. 18 illustrates a close-up transparent angled view of one embodiment of the switch arm 3172 in the switch arm slot 3174 of the cutting forceps shown in FIG. 16. In the illustrated embodiment, the ramp 3304 is in the wall of the switch arm slot 3174 and the protrusion 3302 on the first end of the switch arm 3172 rests on the ramp 3304. The switch arm slot 3174 may be symmetrical, such that there is a ramp on both walls of the switch arm slot 3174, with correspondingly symmetrical protrusions 3302 on the first end of the switch arm 3172.

Figure 19:
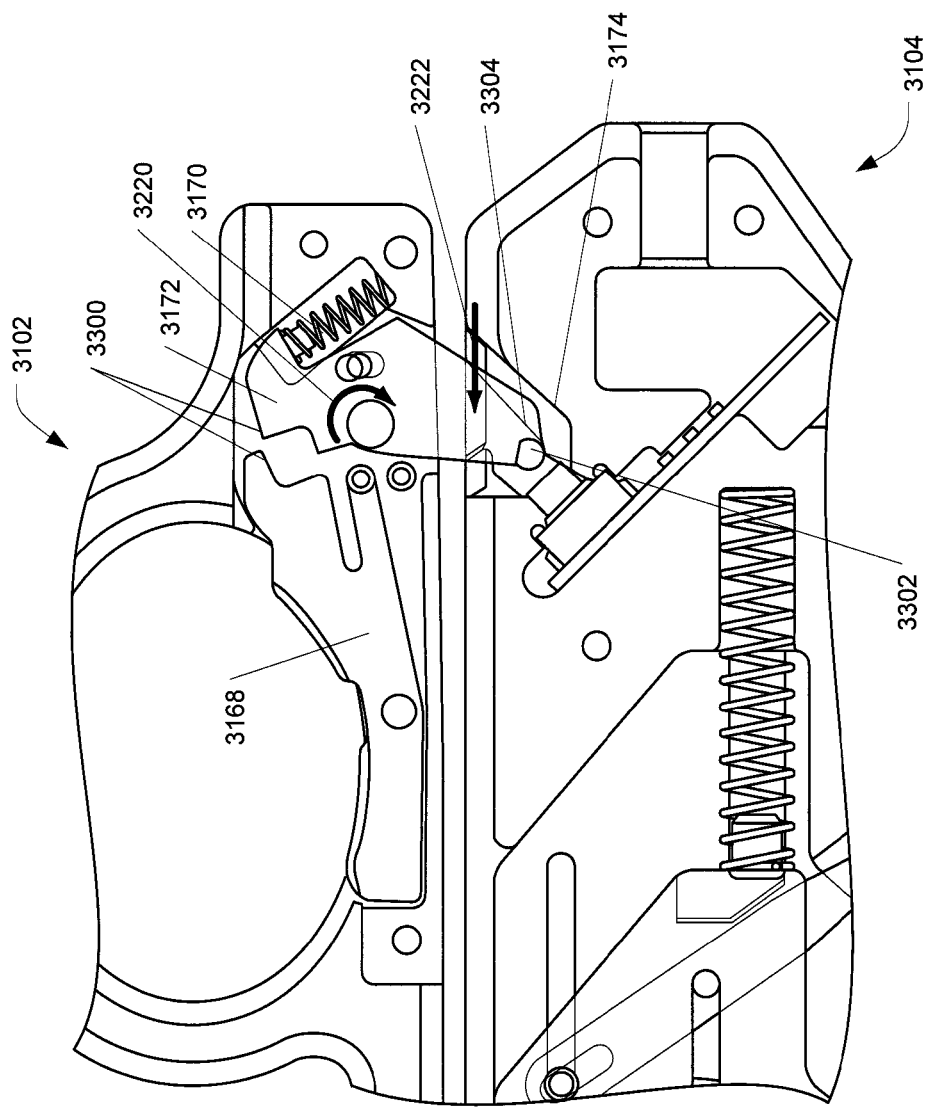
FIG. 19 illustrates a close-up sideways transparent view of the proximal end of the cutting forceps shown in FIG. 16 and the effect of the ramp or guide in the switch arm slot.

FIG. 19 illustrates a close-up sideways transparent view of the proximal end of the cutting forceps 3100 shown in FIG. 16 and the effect of the ramp or guide 3304 in the switch arm slot 3174. As the arms 3102, 3104 of the cutting forceps 3100 are closed, the guide 3304 directs 3222 the first end of the switch arm 1164 towards the distal end of the device. In the illustrated embodiment, the protrusion 3302 rides along the ramp 3304 in a distal direction. The switch arm 3172 is pivotally mounted, and thus rotates 3220, applying pressure on the lock spring 3170. The rotation 3220 of the switch arm 3172 also removes the first contact point 3300, thus unlocking the lock button 3168.

Figure 20:
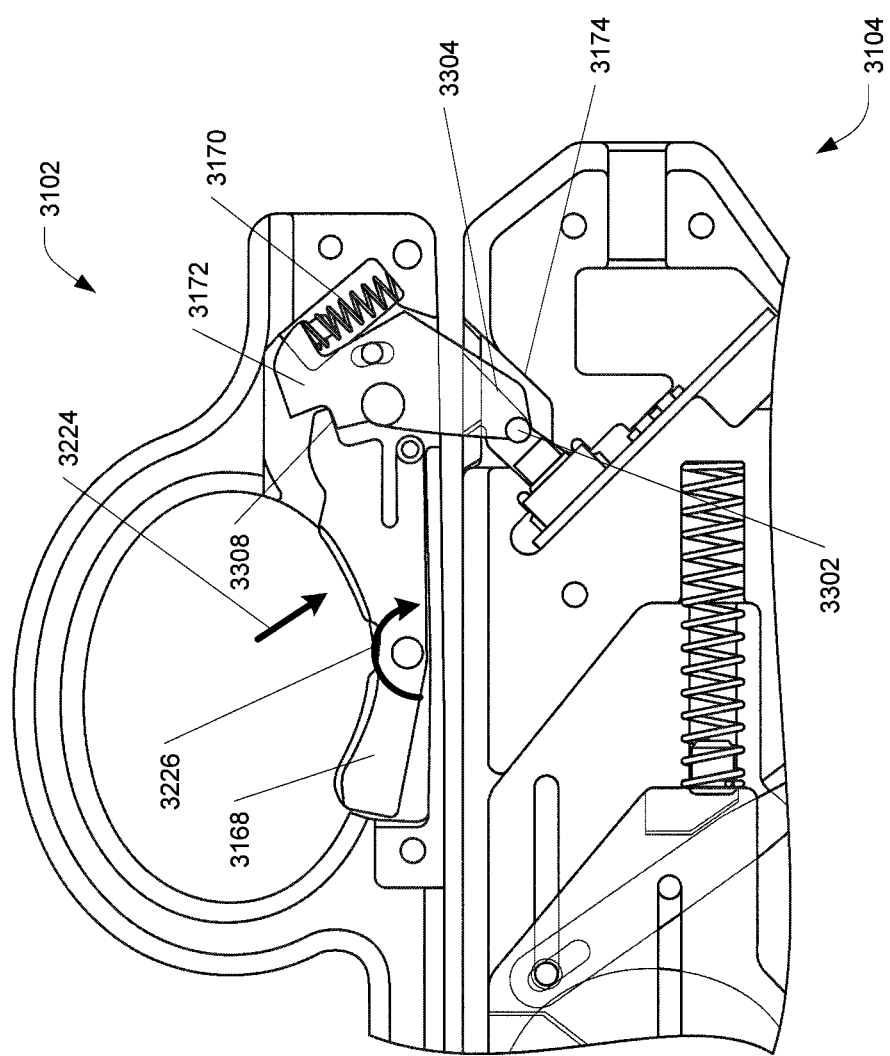
FIG. 20 illustrates a close-up sideways transparent view of a portion of the proximal end of the cutting forceps shown in FIG. 16, illustrating the activation of the lock button.

FIG. 20 illustrates a close-up sideways transparent view of a portion of the proximal end of the cutting forceps 3100 shown in FIG. 16, illustrating a second position of the lock button 3168. The lock button 3168 can be activated by applying pressure 3224 on the proximal end. The lock button 3168 is pivotally mounted within the upper arm 3102, and thus as pressure 3224 is applied to the proximal end of the lock button 3168 the lock button 3168 rotates 3226. As it rotates 3266, the proximal end of the lock button 3168 reaches a second contact point 3308 on the switch arm 3172. The second contact point 3308 prevents the switch arm 3172 from being rotated by the force of the lock spring 3170, thus locking the switch arm 3172 in position and allowing the cutting forceps 3100 to be locked in a closed position.

Figure 21:
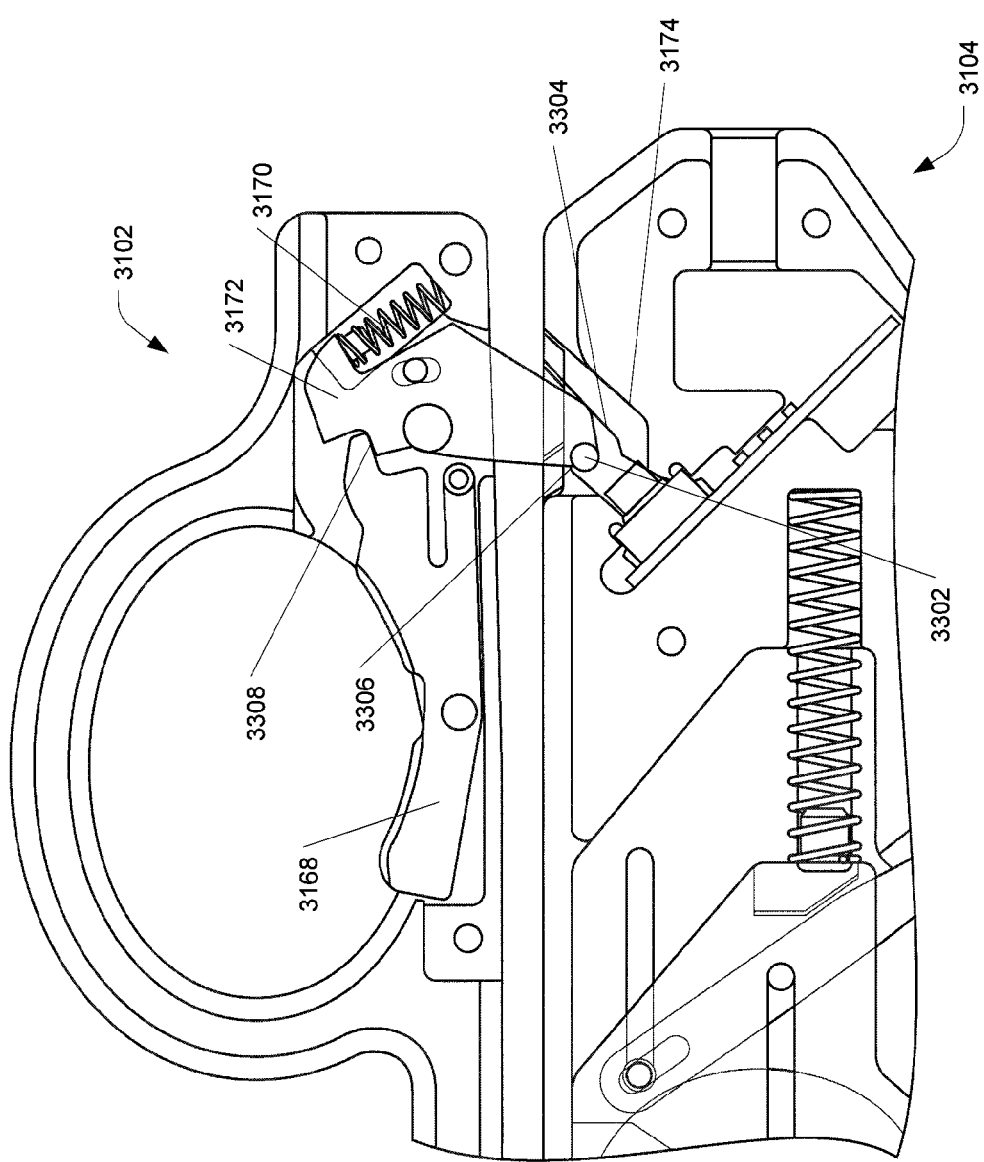
FIG. 21 illustrates a close-up sideways transparent view of the proximal end of the cutting forceps, illustrating how the cutting forceps shown in FIG. 16 can be locked in a closed position.

FIG. 21 illustrates a close-up sideways transparent view of the proximal end of the cutting forceps 3100 shown in FIG. 16, illustrating how the cutting forceps 3100 can be locked in a closed position. Once the lock button 3168 has reached the second position, thus locking the switch arm 3172 by way of the second contact point 3308, the protrusion 3302 on the end of the switch arm 3172 may now make contact with a lip 3306 on the inside of the switch arm slot 3174. The lip 3306 prevents the switch arm 3172 from exiting the switch arm slot 3174, thus locking the arms 3102, 3104 of the cutting forceps 3100 in the closed position.

Figure 22:
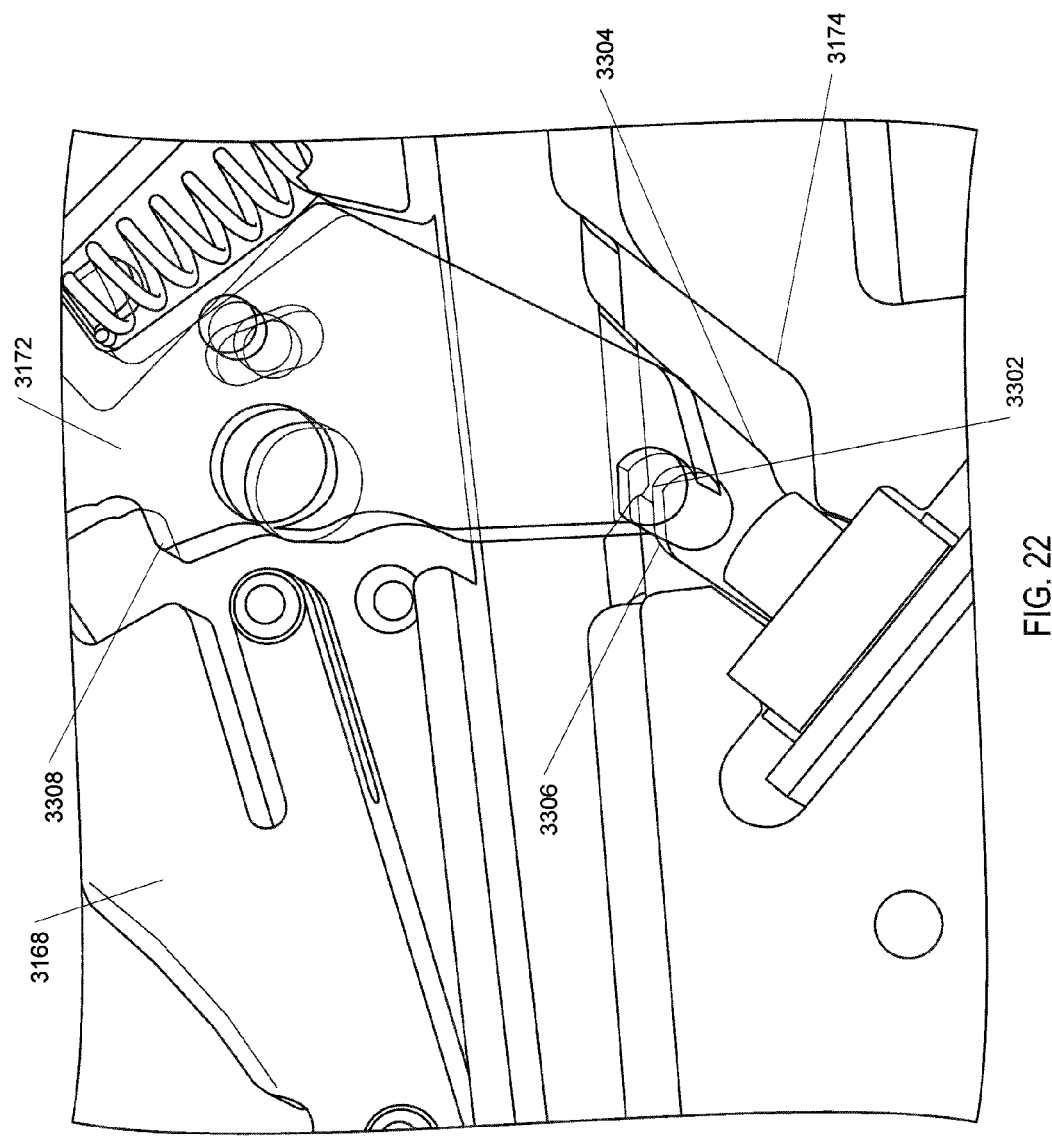
FIG. 22 illustrates a close-up transparent angled view of the switch arm making contact with the lip in the switch arm slot of the cutting forceps shown in FIG. 16.

FIG. 22 illustrates a close-up transparent angled view of the switch arm 3172 making contact with the lip 3306 in the switch arm slot 3174 of the cutting forceps shown in FIG. 16. The lip 3306 is located such that the first end of the switch arm 3172 can only make contact with the lip 3306 after the switch arm 3172 has been rotated by the guide 3304 and the downward force on upper arm 3102. Once the first end is in contact with the lip 3306, the switch arm 3172 is prevented from rotating out from under the lip 3306 by the lock button's 3168 contact with the switch arm 3172 at the second contact point 3308.

Figure 23:
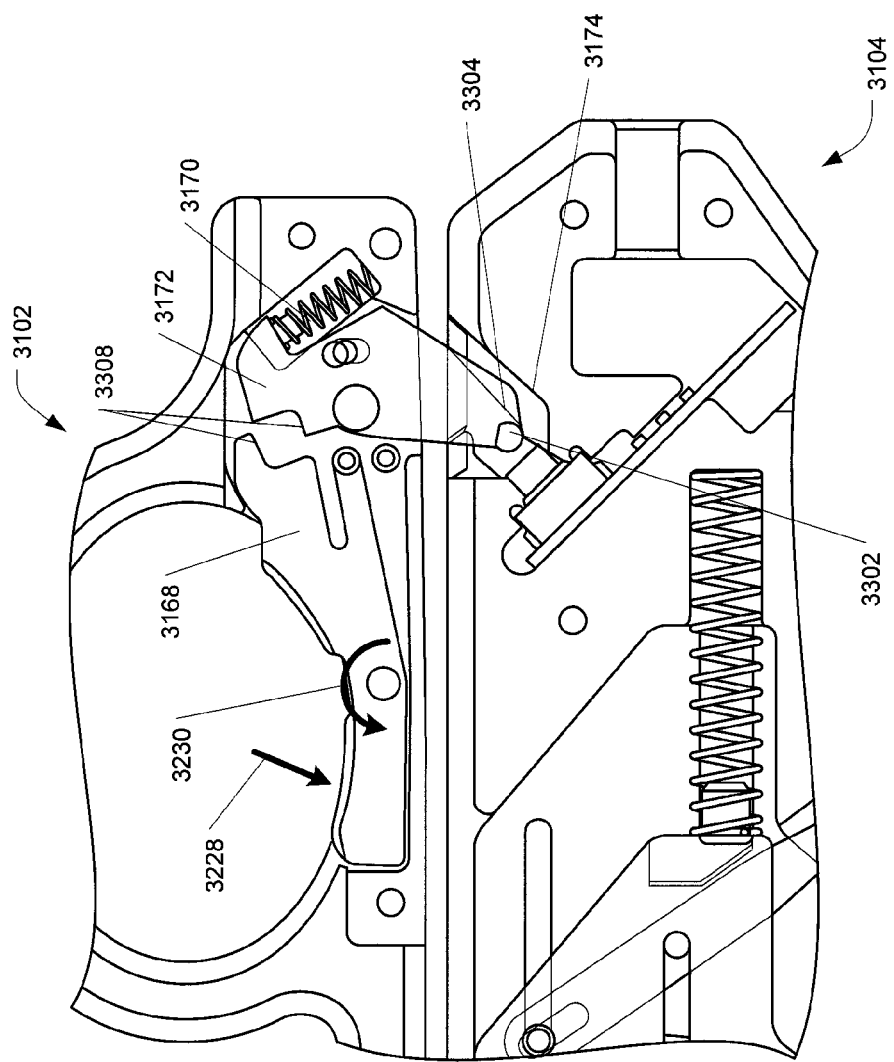
FIG. 23 illustrates a close-up sideways transparent view of a portion of the proximal end of the cutting forceps shown in FIG. 16, illustrating how the arms of the cutting forceps may be unlocked.

FIG. 23 illustrates a close-up sideways transparent view of a portion of the proximal end of the cutting forceps 3100 shown in FIG. 16, illustrating how the arms 3102, 3104 of the cutting forceps 3100 may be unlocked. By applying pressure 3228 on the distal end of the lock button 3168, the lock button can be made to rotate 3230 from the second position to the first position, such that the second contact point 3308 is removed. Removing the second contact point 3308 allows the switch arm 3172 to be driven by the lock spring 3170 back to the neutral position. Once in the neutral position, the switch arm 3172 can exit the switch arm slot 3174.

Figure 24:
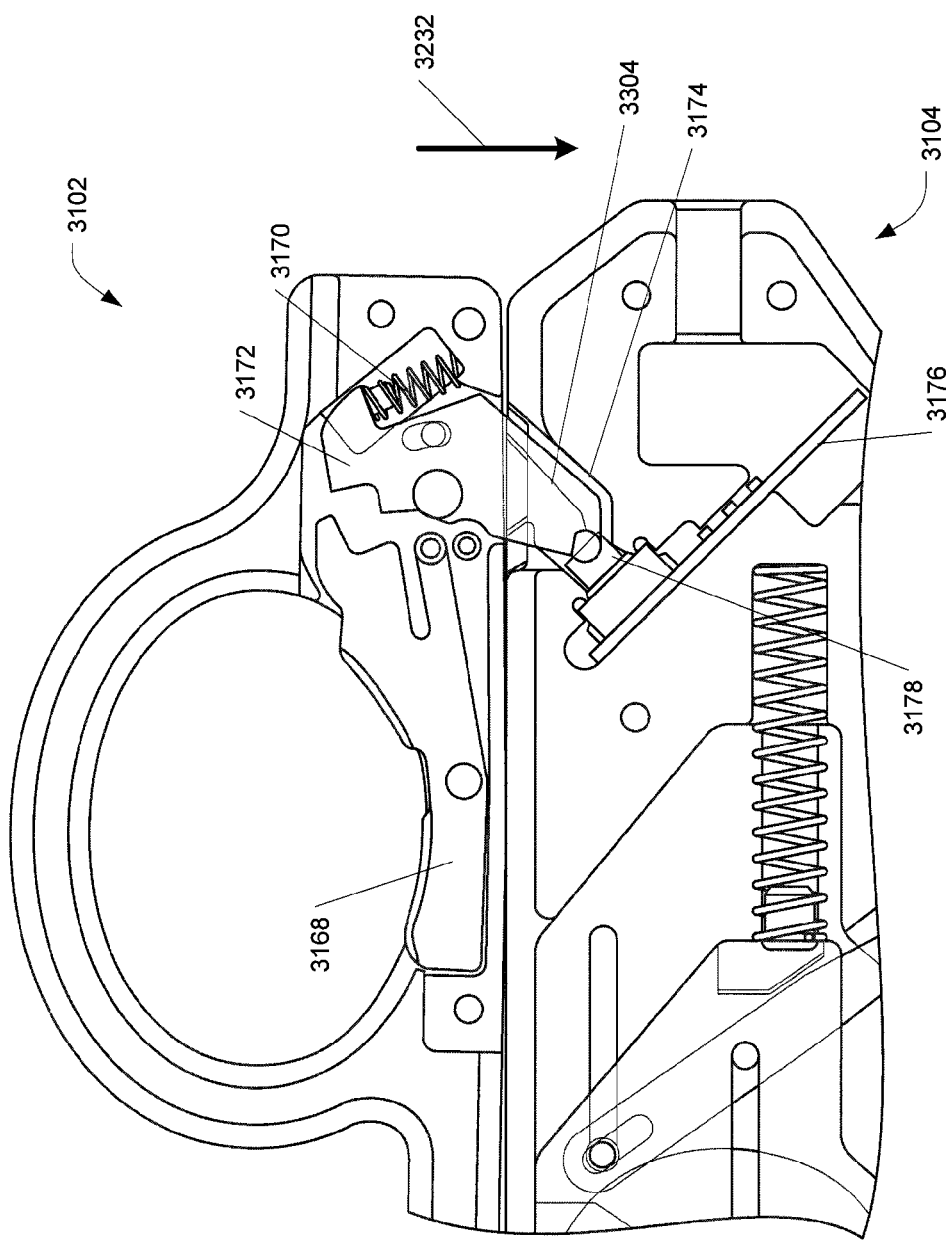
FIG. 24 illustrates as close-up sideways transparent view of one embodiment of a cutting forceps shown in FIG. 16 where the switch arm can be used to activate, or assist in activating, an RF sealing mechanism.

In some embodiments the switch arm 3172 can also be used to activate, or assist in activating, the RF sealing mechanism. FIG. 24 illustrates as close-up sideways transparent view of one such embodiment. As illustrated, the lower arm 3104 may comprise a compression circuit 3176 and a compression circuit button 3178. The compression circuit button 3178 may be positioned near the bottom of the switch arm slot 3174. The guide 3304 in the switch arm slot 3174 may change angle near the bottom of the switch arm slot 3174 such that the force required to close the arms 3102, 3104 of the cutting forceps 3100 is not enough for the switch arm 3172 to reach the bottom of the switch arm slot 3174. That is, additional force is required to overcome the additional angle of the guide 3304. Such force can be applied by compressing 3232 the arms 3102, 3104 of the cutting forceps 3100 closer together. Once the additional angle of the guide 3304 is overcome, the switch arm 3172 may make contact with the compression circuit button 3178 thus activating the compression circuit 3176. In some embodiments it may not be desirable to lock the switch arm 3172 in a position where the compression circuit 3176 is continually activated, instead requiring additional pressure for the switch arm 3172 to reach the compression circuit button 3178. In other embodiments it may be desirable to lock the switch arm 3172 such that the compression circuit 3176 is active so long as the cutting forceps 3100 are closed; this may be accomplished, for example, with the lock button 3168.

It should be noted that, while the trigger lockout mechanism and the RF energy activation mechanism are described as using similar elements, it is understood that not all embodiments require all the elements described. In some embodiments, only a trigger lockout mechanism is desired. Such embodiments may comprise the lock button 3168, the lock spring 3170, the switch arm 3172, and the switch arm slot 3174. In other embodiments, only an RF energy activation mechanism is desired. Such embodiments may comprise the switch arm 3172, the switch arm slot 3174, the compression circuit 3176, and the compression circuit button 3178. In yet other embodiments, it may be desirable to have both the trigger lockout mechanism and the RF energy mechanism. Such embodiment may comprise some or all of the parts described.

Figure 25:
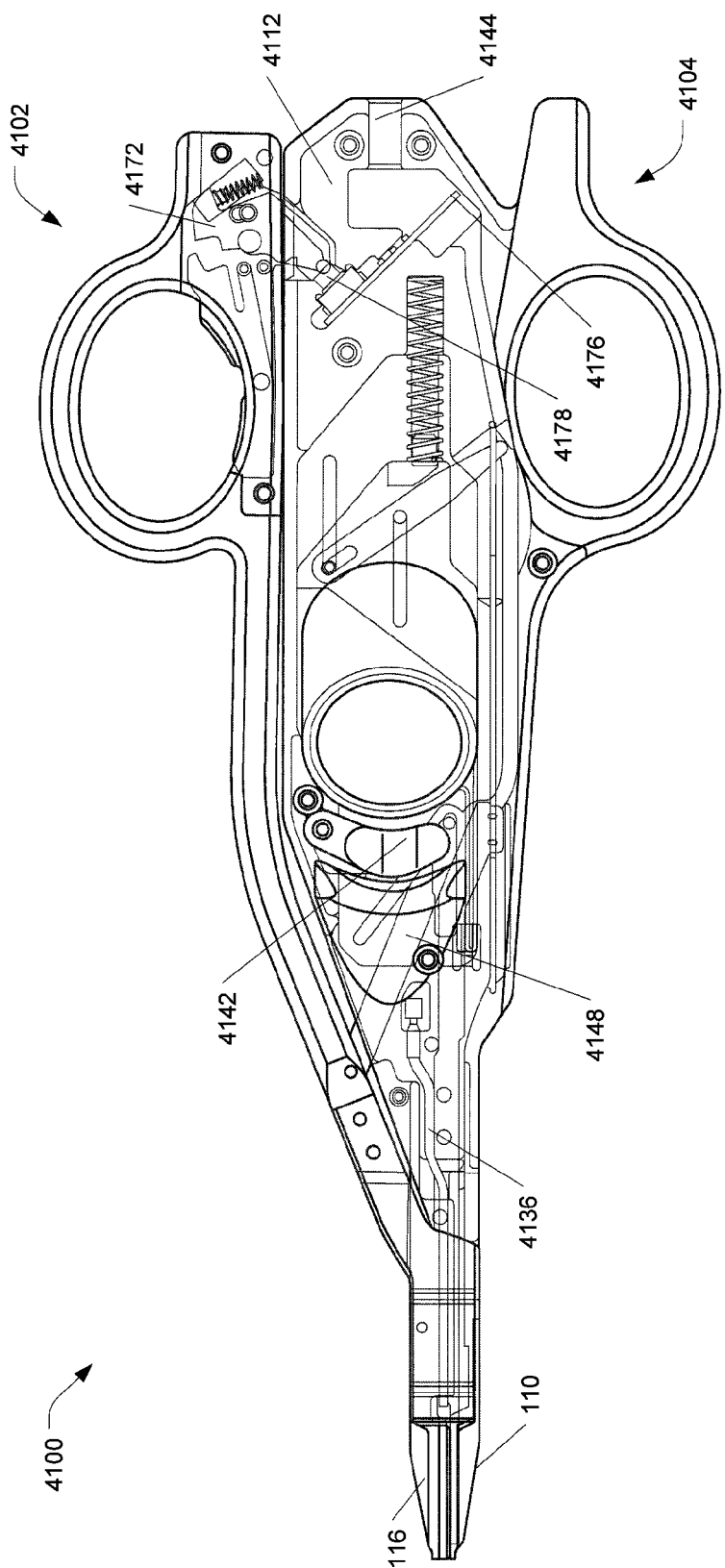
FIG. 25 illustrates the various components of any of the cutting forceps shown herein that may provide for different RF energy activation schemes.

Various embodiments of the cutting forceps may provide different RF energy activation schemes. FIG. 25 illustrates the various components of any of the cutting forceps shown herein that may provide for different RF energy activation schemes. The illustrated components may or may not all appear in the same embodiment, as described below. FIG. 25 illustrates a sideways transparent view of a cutting forceps 4100. The cutting forceps 4100 is similar to the cutting forceps 100 of FIGS. 1-6. As illustrated in FIG. 25, the cutting forceps 4100 comprises an upper arm 4102 pivotally connected to a lower arm 4104. The upper arm 4102 is connected to a lower jaw 4110. The lower arm 4104 comprises a lower arm body 4112 and an upper jaw 4116. The lower arm body 4112 comprises an electrode 4136 for supplying RF energy, wherein the electrode 4136 extends from the lower arm body 4112 along the length of the jaws 4110, 4116.

In one embodiment of the cutting forceps 4100, the RF energy activation scheme uses an energy button 4142, an energy button circuit (not visible), a compression circuit 4176, and a compression circuit button 4178. The compression circuit 4176 is activated by a switch arm 4172 as described above. In a first RF energy activation scheme, the energy button 4142 and energy button circuit 4140 activate the electrode 4136 to deliver RF energy. Activation of compression circuit button 4178 and compression circuit 4176 activates an end tone or seal completion signal, but is not otherwise required to activate the RF energy.

In one embodiment of the cutting forceps 4100, the RF energy activation scheme uses an energy button 4142, an energy button circuit (not visible), a compression circuit 4176, and a compression circuit button 4178. In a second RF energy activation scheme, both the energy button circuit 4140 and the compression circuit 4176 must be activated in order to activate the RF energy. In such embodiments an end tone or seal complete signal may depend on the impedance of tissue held between the jaws 4110, 4116.

In one embodiment of the cutting forceps 4100, the RF energy activation scheme uses an energy button 4142, an energy button circuit (not visible), a compression circuit 4176, and a compression circuit button 4178. In a third RF energy activation scheme, the compression circuit button 4178 and the compression circuit 4176 activate the RF energy. In such a scheme, the energy activation button 4142 and energy button circuit 4140 need not be provided. In such embodiments an end tone or seal complete signal may depend on the impedance of tissue held between the jaws 4110, 4116.

Figure 26A:
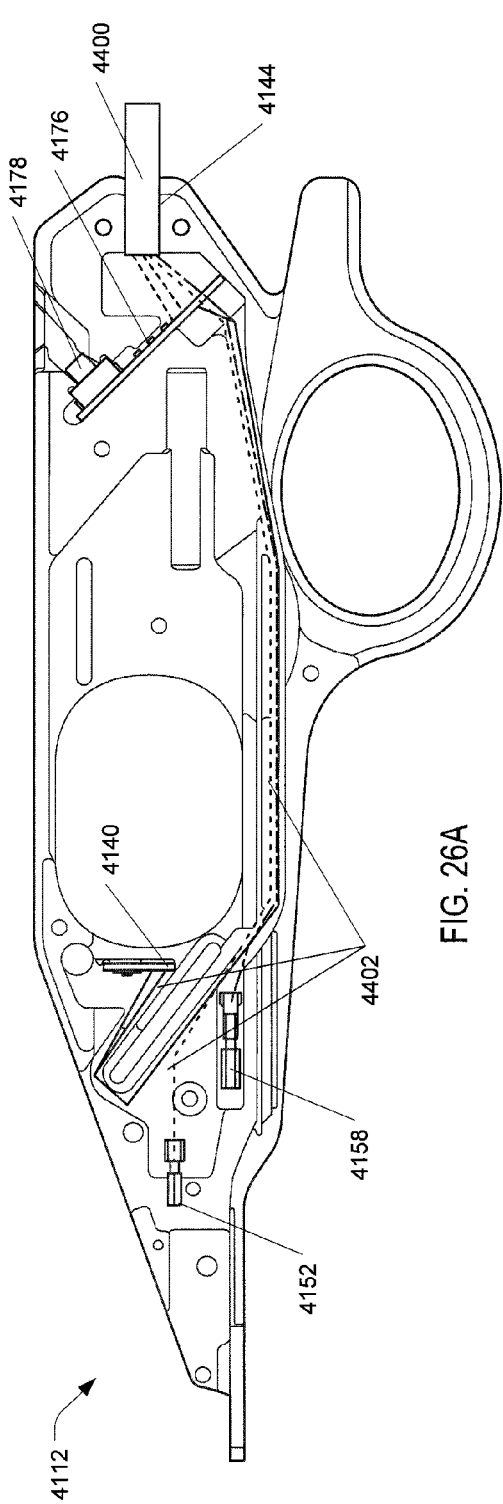
FIG. 26A illustrates one embodiment of an electrical circuit that may provide the necessary power to generate RF energy.

FIG. 26A illustrates one embodiment of an electrical circuit that may provide the necessary power to activate and generate the RF energy. In some embodiments, the cutting forceps 4100 may be provided with power from an external power source. The external power source is connected to the cutting forceps 4100 by a cable 4400 that connects to a port 4144 located at the proximal end of the lower arm body 4112. Wiring 4402 is provided within the lower arm body 4112 from the port 4144 to the compression circuit 4176, the energy button circuit 4140, an electrode connector 4152 that is connected to the electrode, and a return connector 4158 that comprises the return path for the circuit.

Figure 26C:
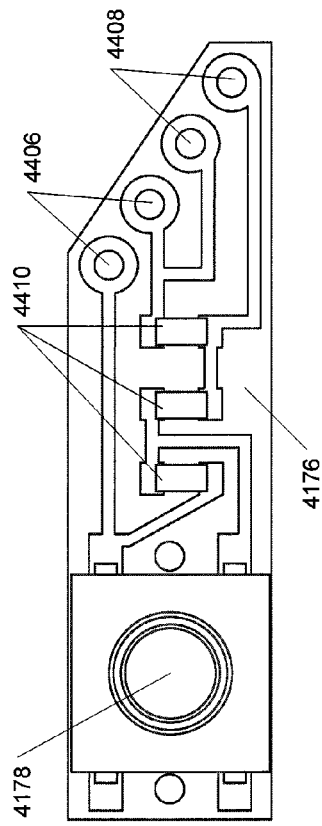
FIG. 26C illustrates one embodiment of a compression circuit.
Figure 26B:
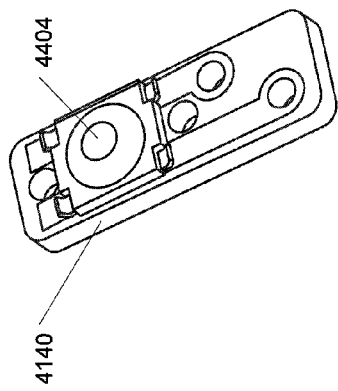
FIG. 26B illustrates one embodiment of the energy button circuit.

FIG. 26B illustrates one embodiment of the energy button circuit 4140. The energy button circuit 4140 comprises a distal energy button 4404, so called for the energy button circuit's 4140 location towards the distal end of the device. The distal energy button 4404 is activated by the energy button 4142, which completes the circuit that provides power to the electrode 4136.

FIG. 26C illustrates one embodiment of a compression circuit 4176. In some embodiments, the compression circuit 4176 operates in tandem with the energy button circuit 4140. For example, in the example illustrated by FIG. 26C, the compression circuit 4176 comprises connections 4406 to the power source as well as connections 4408 to the energy button circuit. In such embodiments, the circuit is complete only if both the compression circuit button 4178 and the distal energy button 4404 are activated. In some embodiments the energy button circuit 4140 is not required; in such cases the compression circuit 4176 may only comprise connections 4406 to the power source. The compression circuit 4176 may also comprise one or more resistors 4410.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

What is claimed is:

1. An electrosurgical instrument for operating on tissue, comprising:
   a first arm, comprising a first handle and a first jaw;
   a second arm pivotally connected to the first arm, the second arm comprising
   a second handle;
   a second jaw comprising an electrode operable to deliver radio frequency (RF) energy to tissue;
   a knife configured to translate within slots defined in the first and second jaws; and
   a push plate operably connected to the knife such that a proximal motion of the push plate extends the knife and a distal motion of the push plate retracts the knife; and
   a trigger lock mechanism comprising a switch arm pivotally mounted to the first arm, the switch arm comprising a first end and a second end, wherein the first end extends below the first arm and is received by a slot integrated into a lower arm of the switch arm, the trigger lock mechanism configured to prevent the first and second jaws from being opened.

2. The electrosurgical instrument of claim 1, comprising a pull ring integrated into the push plate for operating the knife.

3. The electrosurgical instrument of claim 1, wherein the first end of the switch arm comprises a protrusion.

4. The electrosurgical instrument of claim 1, wherein the slot comprises a guide configured to direct the first end of the switch arm in a distal direction, the slot further comprising a lip at a distal side, the lip configured to prevent the first end of the switch arm from exiting the slot.

5. The electrosurgical instrument of claim 4, wherein the first end of the switch arm comprises a protrusion, and wherein the guide comprises a ramp upon which the protrusion rides.

6. The electrosurgical instrument of claim 1, comprising a lock spring, wherein the second end of the switch arm rests against the lock spring and wherein the lock spring is configured to return the switch arm to a neutral position.

7. An electrosurgical instrument for operating on tissue, comprising:
a first arm, comprising a first handle and a first jaw;
a second arm pivotally connected to the first arm, the second arm comprising:
a second handle;
a second jaw comprising an electrode operable to deliver radio frequency (RF) energy to tissue;
a knife configured to translate within slots defined in the first and second jaws; and
a push plate operably connected to the knife such that a proximal motion of the push plate extends the knife and a distal motion of the push plate retracts the knife; and
a trigger lock mechanism comprising a switch arm pivotally mounted to the first arm, the switch arm comprising a first end and a second end, wherein the first end extends below the first arm, the trigger lock mechanism configured to prevent the first and second jaws from being opened;
wherein the first end of the switch arm comprises a lock button pivotally mounted inside the first handle and wherein the switch arm is movable between a first position and a second position, wherein the second position prevents the switch arm from returning to a neutral position.

8. The electrosurgical instrument of claim 7, wherein the switch arm is configured to prevent the lock button from transitioning between the first position and the second position when the switch arm is in the neutral position.

9. The electrosurgical instrument of claim 1, the second arm further comprising an energy button configured to activate the RF energy.

10. An electrosurgical instrument for operating on tissue, comprising:
a first arm comprising a first handle and a first jaw;
a second arm pivotally connected to the first arm, the second arm comprising:
a second handle;
a second jaw comprising an electrode operable to deliver radio frequency (RF) energy to tissue;
a knife configured to translate within slots defined in the first and second jaws;
a push plate operably connected to the knife such that a proximal motion of the push plate extends the knife and a distal motion of the push plate retracts the knife; and
a trigger lock mechanism configured to prevent the first and second jaws from being opened;
a switch arm; and
a switch arm slot comprising a base;
the second arm further comprising a compression circuit and a compression button for activating the compression circuit, wherein the compression button is located at the base of the switch arm slot and is activated by pressure applied by the switch arm.

11. The electrosurgical instrument of claim 10, comprising a pull ring integrated into the push plate for operating the knife.

12. The electrosurgical instrument of claim 10, wherein the second arm comprises an energy button.

13. The electrosurgical instrument of claim 12, wherein the energy button is configured to activate the RF energy and the compression circuit is configured to enable an end tone.

14. The electrosurgical instrument of claim 12, wherein the RF energy is activated only when both the energy button and the compression circuit are activated simultaneously.

15. The electrosurgical instrument of claim 12, wherein the energy button is configured to activate the RF energy and the compression circuit is configured to activate the RF energy.

16. The electrosurgical instrument of claim 10, wherein the compression circuit is configured to enable the RF energy.

17. An electrosurgical instrument for operating on tissue, comprising:
a first arm comprising a first handle and a first jaw;
a second arm pivotally connected to the first arm, the second arm comprising:
a second handle;
a second jaw comprising an electrode operable to deliver radio frequency (RF) energy to tissue;
a knife configured to translate within slots defined in the first and second jaws;
a pull ring;
a push plate operably connected to the knife such that a proximal motion of the push plate extends the knife and a distal motion of the pull ring retracts the knife;
a compression circuit; and
a compression circuit button configured to activate the compression circuit.

18. The electrosurgical instrument of claim 17, wherein the pull ring is integrated into the push plate for operating the knife.

19. The electrosurgical instrument of claim 17, comprising:
a switch arm pivotally mounted to the first arm, the switch arm comprising a first end and a second end, wherein the first end extends below the first arm; and
a switch arm slot integrated into the second arm and configured to accept the first end of the switch arm;
wherein the compression circuit button is located at a base of the switch arm slot and is activated by pressure applied by the switch arm.

20. The electrosurgical instrument of claim 19, wherein the switch arm is configured to require extra pressure on the first arm for the switch arm to activate the compression circuit button.

21. The electrosurgical instrument of claim 17, comprising an energy button.

22. The electrosurgical instrument of claim 21, wherein the energy button is configured to activate the RF energy and the compression circuit is configured to enable an end tone.

23. The electrosurgical instrument of claim 21, wherein the RF energy is activated only when both the energy button and the compression circuit are activated simultaneously.

24. The electrosurgical instrument of claim 21, wherein the energy button is configured to activate the RF energy and the compression circuit is configured to activate the RF energy.

25. The electrosurgical instrument of claim 17, wherein the compression circuit is configured to enable the RF energy.

* * * * *